United States Patent
Yin et al.

(10) Patent No.: US 10,190,151 B2
(45) Date of Patent: *Jan. 29, 2019

(54) HIGH-THROUGHPUT AND HIGHLY MULTIPLEXED IMAGING WITH PROGRAMMABLE NUCLEIC ACID PROBES

(71) Applicant: President and Fellows of Harvard College, Cambridge, MA (US)

(72) Inventors: Peng Yin, Brookline, MA (US); Sarit Agasti, Jakkur (IN); Xi Chen, West Newton, MA (US); Ralf Jungmann, Munich (DE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,031

(22) Filed: Mar. 23, 2018

(65) Prior Publication Data
US 2018/0216159 A1    Aug. 2, 2018

Related U.S. Application Data

(63) Continuation of application No. 15/108,911, filed as application No. PCT/US2015/020034 on Mar. 11, 2015.

(60) Provisional application No. 61/951,461, filed on Mar. 11, 2014.

(51) Int. Cl.
C12Q 1/68 (2018.01)
C12Q 1/6804 (2018.01)
C12Q 1/6818 (2018.01)

(52) U.S. Cl.
CPC ......... *C12Q 1/6804* (2013.01); *C12Q 1/6818* (2013.01)

(58) Field of Classification Search
None
See application file for complete search history.

(56) References Cited

U.S. PATENT DOCUMENTS

| | | |
|---|---|---|
| 6,083,486 A | 7/2000 | Weissleder et al. |
| 6,150,173 A | 11/2000 | Schubert |
| 6,534,041 B1 | 3/2003 | Licha et al. |
| 6,833,246 B2 | 12/2004 | Balasubramanian |
| 6,924,115 B2 | 8/2005 | Schubert |
| 7,371,520 B2 | 5/2008 | Zhao et al. |
| 7,838,302 B2 | 11/2010 | Zhuang et al. |
| 8,481,714 B2 | 7/2013 | Fujimoto et al. |
| 9,944,972 B2 * | 4/2018 | Yin ............... C12Q 1/6804 |
| 10,024,796 B2 | 7/2018 | Lin et al. |
| 2002/0106648 A1 | 8/2002 | Lizardi et al. |
| 2002/0173053 A1 | 11/2002 | Damaj et al. |
| 2002/0177149 A1 | 11/2002 | Rimm et al. |
| 2003/0044353 A1 | 3/2003 | Weissleder et al. |
| 2003/0064398 A1 | 4/2003 | Barnes |
| 2003/0073149 A1 | 4/2003 | Archer et al. |
| 2004/0121382 A1 | 6/2004 | Liu et al. |
| 2004/0121385 A1 | 6/2004 | Andersson et al. |
| 2004/0248325 A1 | 12/2004 | Bukusoglu |
| 2005/0074781 A1 | 4/2005 | Von Schroeder et al. |
| 2005/0169843 A1 | 8/2005 | Weissleder et al. |
| 2005/0171434 A1 | 8/2005 | Madden et al. |
| 2005/0287578 A1 | 12/2005 | Davis |
| 2006/0063196 A1 | 3/2006 | Akeson et al. |
| 2006/0199216 A1 | 9/2006 | Su et al. |
| 2006/0252079 A1 | 11/2006 | Oldham et al. |
| 2006/0292616 A1 | 12/2006 | Neely et al. |
| 2007/0048759 A1 | 3/2007 | Luo et al. |
| 2007/0117109 A1 | 5/2007 | Rothemund |
| 2008/0032307 A1 | 2/2008 | Buzby et al. |
| 2008/0118934 A1 | 5/2008 | Gerdes et al. |
| 2008/0287668 A1 | 11/2008 | Toth-Fejel et al. |
| 2009/0011956 A1 | 1/2009 | Yin et al. |
| 2010/0015607 A1 | 1/2010 | Geiss et al. |
| 2010/0069621 A1 | 3/2010 | Maune et al. |
| 2010/0081134 A1 | 4/2010 | Mirkin et al. |
| 2010/0216978 A1 | 8/2010 | Shih |
| 2012/0004132 A1 | 1/2012 | Zhang et al. |
| 2012/0022244 A1 | 1/2012 | Yin |
| 2012/0178081 A1 | 7/2012 | Nguyen et al. |
| 2012/0252685 A1 | 10/2012 | Treynor et al. |
| 2013/0072390 A1 | 3/2013 | Wang et al. |
| 2013/0261019 A1 | 10/2013 | Lin et al. |
| 2014/0038201 A1 | 2/2014 | Zhuang et al. |
| 2014/0349288 A1 | 11/2014 | Church et al. |
| 2016/0319328 A1 | 11/2016 | Yin et al. |

(Continued)

FOREIGN PATENT DOCUMENTS

| | | |
|---|---|---|
| DE | 4421891 A1 | 1/1996 |
| JP | 2003-259869 A | 9/2003 |
| WO | WO 00/03034 A2 | 1/2000 |

(Continued)

OTHER PUBLICATIONS

[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.

(Continued)

*Primary Examiner* — James Martinell

(74) *Attorney, Agent, or Firm* — Wolf, Greenfield & Sacks, P.C.

(57) ABSTRACT

The present invention provides, inter alia, methods and compositions for imaging, at high spatial resolution, targets of interest.

22 Claims, 7 Drawing Sheets

Specification includes a Sequence Listing.

(56) References Cited

U.S. PATENT DOCUMENTS

2017/0137864 A1    5/2017    Yin et al.

FOREIGN PATENT DOCUMENTS

| WO | WO 00/20641 A1 | 4/2000 |
|---|---|---|
| WO | WO 00/58507 A1 | 10/2000 |
| WO | WO 01/94625 A2 | 12/2001 |
| WO | WO 02/079771 A1 | 10/2002 |
| WO | WO 2005/017485 A2 | 2/2005 |
| WO | WO 2007/076128 A2 | 7/2007 |
| WO | WO 2007/117256 A1 | 10/2007 |
| WO | WO 2012/058638 A2 | 5/2012 |
| WO | WO 2012/071428 A2 | 5/2012 |
| WO | WO 2014/028538 A2 | 2/2014 |
| WO | WO 2014/071361 A1 | 5/2014 |
| WO | WO 2014/130388 A1 | 8/2014 |
| WO | WO 2014/135838 A1 | 9/2014 |
| WO | WO 2015/089506 A2 | 6/2015 |
| WO | WO 2015/138653 A1 | 9/2015 |

OTHER PUBLICATIONS

[No Author Listed], New England Biolabs, Inc. 2013-14 Catalog and Technical Reference, User Enzyme, 2013, p. 129.

Abulrob et al., Nanoscale imaging of epidermal growth factor receptor clustering: effects of inhibitors. J Biol Chem. Jan. 29, 2010;285(5):3145-56. doi: 10.1074/jbc.M109.073338. Epub Dec. 3, 2009.

Agasti et al., DNA-barcoded labeling probes for highly multiplexed Exchange-PAINT imaging. Chem Sci. Apr. 1, 2017;8(4):3080-91. doi: 10.1039/c6sc05420j. Epub Jan. 30, 2017.

Agasti et al., Photocleavable DNA barcode-antibody conjugates allow sensitive and multiplexed protein analysis in single cells. J Am Chem Soc. Nov. 14, 2012;134(45):18499-502. doi:10.1021/ja307689w. Epub Nov. 2, 2012.

Anderson et al., Improved fluoroimmunoassays using the dye Alexa Fluor 647 with the RAPTOR, a fiber optic biosensor. J Immunol Methods. Dec. 20, 2002;271(1-2):17-24.

Asanuma et al., Enantioselective Incorporation of Azobenzenes into Oligodeoxyribonucleotide for Effective Photoregulation of Duplex Formation This work was partially supported by a Grant-in-Aid for Scientific Research from the Ministry of Education, Culture, Sports, Science and Technology, Japan (Molecular Synchronization for Design of New Materials System). The support by the Grant from "Research for the Future" Program of the Japan Society for the Promotion of Science JSPS-RFTF97I00301) is also acknowledged. . Angew Chem Int Ed Engl. Jul. 16, 2001;40(14):2671-2673.

Averbuch et al., Two Linear Unmixing Algorithms to Recognize Targets Using Supervised Classification and Orthogonal Rotation in Airborne Hyperspectral Images. Remote Sens. 2012;4(2):532-60.

Bai et al., Cryo-EM structure of a 3D DNA-origami object. Proc Natl Acad Sci U S A. Dec. 4, 2012;109(49):20012-7. doi:10.1073/pnas.1215713109. Epub Nov. 19, 2012.

Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.

Ben-Shem et al., The structure of the eukaryotic ribosome at 3.0 Å resolution. Science. Dec. 16, 2011;334(6062):1524-9. doi: 10.1126/science.1212642. Epub Nov. 17, 2011.

Braeckmans et al., Encoding microcarriers by spatial selective photobleaching. Nat Mater. Mar. 2003;2(3):169-73.

Chapman et al., Femtosecond X-ray protein nanocrystallography. Nature. Feb. 3, 2011;470(7332):73-7. doi: 10.1038/nature09750.

Cheng et al., A primer to single-particle cryo-electron microscopy. Cell. Apr. 23, 2015;161(3):438-49. doi:10.1016/j.cell.2015.03.050.

Chhabra et al., DNA self-assembly for nanomedicine. Adv Drug Deliv Rev. Apr. 30, 2010;62(6):617-25. doi:10.1016/j.addr.2010.03.005. Epub Mar. 15, 2010.

Choi et al., Next-generation in situ hybridization chain reaction: higher gain, lower cost, greater durability. ACS Nano. May 27, 2014;8(5):4284-94. doi: 10.1021/nn405717p. Epub Apr. 8, 2014.

Christensen et al., Role of the Bombyx mori R2 element N-terminal domain in the target-primed reverse transcription (TPRT) reaction. Nucleic Acids Res. Nov. 10, 2005;33(20):6461-8.

Citri et al., EGF-ERBB signalling: towards the systems level. Nat Rev Mol Cell Biol. Jul. 2006;7(7):505-16.

Dejneka et al., Rare earth-doped glass microbarcodes. Proc Natl Acad Sci U S A. Jan. 21, 2003;100(2):389-93. Epub Jan. 6, 2003.

Deng et al., CASFISH: CRISPR/Cas9-mediated in situ labeling of genomic loci in fixed cells. Proc Natl Acad Sci U S A. Sep. 22, 2015;112(38):11870-5. doi: 10.1073/pnas.1515692112. Epub Aug. 31, 2015.

Dirks et al., Triggered amplification by hybridization chain reaction. Proc Natl Acad Sci U S A. Oct. 26, 2004;101(43):15275-8. Epub Oct. 18, 2004.

Douglas et al., DNA-nanotube-induced alignment of membrane proteins for NMR structure determination. Proc Natl Acad Sci U S A. Apr. 17, 2007;104(16):6644-8. Epub Apr. 2, 2007.

Douglas et al., Self-assembly of DNA into nanoscale three-dimensional shapes. Nature. May 21, 2009;459(7245):414-8. doi: 10.1038/nature08016.

Eggeling et al., Photobleaching of Fluorescent Dyes under Conditions Used for Single-Molecule Detection: Evidence of Two-Step Photolysis. Anal Chem. Jul. 1, 1998;70(13):2651-9. doi: 10.1021/ac980027p.

Elshal et al., Multiplex bead array assays: performance evaluation and comparison of sensitivity to ELISA. Methods. Apr. 2006;38(4):317-23.

Fournier-Bidoz et al., Facile and rapid one-step mass preparation of quantum-dot barcodes. Angew Chem Int Ed Engl. 2008;47(30):5577-81. doi: 10.1002/anie.200800409.

Geiss et al., Direct multiplexed measurement of gene expression with color-coded probe pairs. Nat Biotechnol. Mar. 2008;26(3):317-25. doi: 10.1038/nbt1385. Epub Feb. 17, 2008.

Gerdes et al., Highly multiplexed single-cell analysis of formalin-fixed, paraffin-embedded cancer tissue. Proc Natl Acad Sci U S A. Jul. 16, 2013;110(29):11982-7. doi:10.1073/pnas.1300136110. Epub Jul. 1, 2013.

Ghauharali et al., Fluorescence photobleaching-based image standardization for fluorescence microscopy. J Microscopy. May 2000;198(2):88-100.

Gibriel, Options available for labelling nucleic acid samples in DNA microarray-based detection methods. Briefings in Functional Genomics. Apr. 17, 2012;11(4):311-8. doi: 10.1093/bfgp/els015.

Giepmans et al., The fluorescent toolbox for assessing protein location and function. Science. Apr. 14, 2006;312(5771):217-24.

Gietl et al., DNA origami as biocompatible surface to match single-molecule and ensemble experiments. Nucleic Acids Res. Aug. 2012;40(14):e110. doi: 10.1093/nar/gks326. Epub Apr. 20, 2012.

Gonçalves, Fluorescent labeling of biomolecules with organic probes. Chem Rev. Jan. 2009;109(1):190-212. doi:10.1021/cr0783840.

Gudiksen et al., Growth of nanowire superlattice structures for nanoscale photonics and electronics. Nature. Feb. 7, 2002;415(6872):617-20.

Guo et al., Four-color DNA sequencing with 3'-O-modified nucleotide reversible terminators and chemically cleavable fluorescent dideoxynucleotides. Proc Natl Acad Sci U S A. Jul. 8, 2008;105(27):9145-50. doi: 10.1073/pnas.0804023105. Epub Jun. 30, 2008.

Gustafsson et al., Three-dimensional resolution doubling in wide-field fluorescence microscopy by structured illumination. Biophys J. Jun. 2008;94(12):4957-70. doi:10.1529/biophysj.107.120345. Epub Mar. 7, 2008.

Ha et al., Photophysics of fluorescent probes for single-molecule biophysics and super-resolution imaging. Annu Rev Phys Chem. 2012;63:595-617. doi: 10.1146/annurev-physchem-032210-103340. Epub Jan. 30, 2012.

Han et al., Quantum-dot-tagged microbeads for multiplexed optical coding of biomolecules. Nat Biotechnol. Jul. 2001;19(7):631-5.

(56) References Cited

OTHER PUBLICATIONS

Huang et al., Selective photothermal therapy for mixed cancer cells using aptamer-conjugated nanorods. Langmuir. Oct. 21, 2008;24(20):11860-5. doi: 10.1021/la801969c. Epub Sep. 26, 2008.
Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.
Jones et al., Nanomaterials. Programmable materials and the nature of the DNA bond. Science. Feb. 20, 2015;347(6224):1260901. doi:10.1126/science.1260901.
Joo et al., Advances in single-molecule fluorescence methods for molecular biology. Annu Rev Biochem. 2008;77:51-76. doi:10.1146/annurev.biochem.77.070606.101543.
Ju et al., Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014. Supplementary Text and Figures; 38 pages. XP-002775144.
Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.
Jungmann et al., Single-molecule kinetics and super-resolution microscopy by fluorescence imaging of transient binding on DNA origami. Nano Lett. Nov. 10, 2010;10(11):4756-61.
Kato et al., High-resolution structural analysis of a DNA nanostructure by cryoEM. Nano Lett. Jul. 2009;9(7):2747-50. doi: 10.1021/nl901265n.
Ke et al., Self-Assembled Water-Soluble Nucleic Acid Probe Tiles for Label-Free RNA Hybridization Assays. Science. Jan. 11, 2008;319(5860):180-3.
Ke et al., Three-dimensional structures self-assembled from DNA bricks. Science. Nov. 30, 2012;338(6111):1177-83. doi: 10.1126/science.1227268.
Kuzuya et al., Six-helix and eight-helix DNA nanotubes assembled from half-tubes. Nano Lett. Jun. 2007;7(6):1757-63. Epub May 15, 2007.
Levsky et al., Fluorescence in situ hybridization: past, present and future. J Cell Sci. Jul. 15, 2003;116(Pt 14):2833-8.
Levsky et al., Single-cell gene expression profiling. Science. Aug. 2, 2002;297(5582):836-40.
Li et al., Controlled fabrication of fluorescent barcode nanorods. ACS Nano. Aug. 24, 2010;4(8):4350-60. doi: 10.1021/nn9017137.
Li et al., Multiplexed detection of pathogen DNA with DNA-based fluorescence nanobarcodes. Nat Biotechnol. Jul. 2005;23(7):885-9. Epub Jun. 12, 2005.
Lichtman et al., Fluorescence microscopy. Nat Methods. Dec. 2005;2(12):910-9.
Lin et al., Functional DNA nanotube arrays: bottom-up meets top-down. Angewandte Chemie. 2007;119(32):620-4.
Lin et al., Self-assembled combinatorial encoding nanoarrays for multiplexed biosensing. Nano Lett. Feb. 7, 2007;7(2):507-12.
Lin et al., Submicrometre geometrically encoded fluorescent barcodes self-assembled from DNA. Nat Chem. Oct. 2012;4(10):832-9.
Lin et al., Designer DNA nanoarchitectures. Biochemistry. Mar. 3, 2009;48(8):1663-74. doi: 10.1021/bi802324w.
Liu et al., Aptamer-directed self-assembly of protein arrays on a DNA nanostructure. Angew Chem Int Ed Engl. Jul. 11, 2005;44(28):4333-8.
Livet et al., Transgenic strategies for combinatorial expression of fluorescent proteins in the nervous system. Nature. Nov. 1, 2007;450(7166):56-62.
Lubeck et al., Single-cell in situ RNA profiling by sequential hybridization. Nat Methods. Apr. 2014;11(4):360-1. doi:10.1038/nmeth.2892.
Mag et al., Synthesis and selective cleavage of an oligodeoxynucleotide containing a bridged internucleotide 5'-phosphorothioate linkage. Nucleic Acids Res. Apr. 11, 1991;19(7):1437-41.
Marcon et al., 'On-the-fly' optical encoding of combinatorial peptide libraries for profiling of protease specificity. Mol Biosyst. Jan. 2010;6(1):225-33. doi: 10.1039/b909087h. Epub Oct. 6, 2009.
Martin, Functional Synthetic DNA Nanostructures. Dissertation. Technische Universitat München, Laboratory for Biomolecular Nanotechnology. Filed on Mar. 12, 2013.
Mathieu et al., Six-helix bundles designed from DNA. Nano Lett. Apr. 2005;5(4):661-5.
Mei et al., Stability of DNA origami nanoarrays in cell lysate. Nano Lett. Apr. 13, 2011;11(4):1477-82. doi: 10.1021/nl1040836. Epub Mar. 2, 2011.
Meserve et al., A double-stranded molecular probe for homogeneous nucleic acid analysis. Analyst. Aug. 2008;133(8):1013-9. doi:10.1039/b804853c. Epub Jun. 6, 2008.
Mittag et al., Sequential photobleaching of fluorochromes for polychromatic slide-based cytometry. Cytometry A. Mar. 2006;69(3):139-41.
Myhrvold et al., Isothermal self-assembly of complex DNA structures under diverse and biocompatible conditions. Nano Lett. Sep. 11, 2013;13(9):4242-8. doi: 10.1021/nl4019512. Epub Aug. 26, 2013.
Nannenga et al., High-resolution structure determination by continuous-rotation data collection in MicroED. Nat Methods. Sep. 2014;11(9):927-30. doi: 10.1038/nmeth.3043. Epub Aug. 3, 2014.
Nannenga et al., Protein structure determination by MicroED. Curr Opin Struct Biol. Aug. 2014;27:24-31. doi: 10.1016/j.sbi.2014.03.004. Epub Apr. 5, 2014.
Nicewarner-Pena et al., Submicrometer metallic barcodes. Science. Oct. 5, 2001;294(5540):137-41.
Pinheiro et al., Challenges and opportunities for structural DNA nanotechnology. Nat Nanotechnol. Nov. 6, 2011;6(12):763-72. doi:10.1038/nnano.2011.187.
Raj et al., Imaging individual mRNA molecules using multiple singly labeled probes. Nat Methods. Oct. 2008;5(10):877-9. doi: 10.1038/nmeth.1253. Epub Sep. 21, 2008.
Rajendran et al., Selection of fluorescent aptamer beacons that light up in the presence of zinc. Anal Bioanal Chem. Feb. 2008;390(4):1067-75. Epub Nov. 30, 2007.
Resch-Genger et al., Quantum dots versus organic dyes as fluorescent labels. Nat Methods. Sep. 2008;5(9):763-75. doi: 10.1038/nmeth.1248.
Rinker et al., Self-assembled DNA nanostructures for distance-dependent multivalent ligand-protein binding. Nat Nanotechnol. Jul. 2008;3(7):418-22. doi: 10.1038/nnano.2008.164. Epub Jun. 22, 2008.
Rodgers et al., Transient association of Ku with nuclear substrates characterized using fluorescence photobleaching. J Immunol. Mar. 1, 2002;168(5):2348-55.
Rosi et al., Nanostructures in biodiagnostics. Chem Rev. Apr. 2005;105(4):1547-62.
Rothemund, Folding DNA to create nanoscale shapes and patterns. Nature. Mar. 16, 2006;440(7082):297-302.
Sadowski et al., Developmental self-assembly of a DNA tetrahedron. ACS Nano. Apr. 22, 2014;8(4):3251-9. doi:10.1021/nn4038223. Epub Apr. 11, 2014.
Schmied et al., DNA origami-based standards for quantitative fluorescence microscopy. Nat Protoc. 2014;9(6):1367-91. doi: 10.1038/nprot.2014.079. Epub May 15, 2014.
Schubert et al., Analyzing proteome topology and function by automated multidimensional fluorescence microscopy. Nat Biotechnol. Oct. 2006;24(10):1270-8. Epub Oct. 1, 2006.
Schweller et al., Multiplexed in situ immunofluorescence using dynamic DNA complexes. Angew Chem Int Ed Engl. Sep. 10, 2012;51(37):9292-6. doi:10.1002/anie.201204304. Epub Aug. 15, 2012.
Seeman, Nucleic acid junctions and lattices. J Theor Biol. Nov. 21, 1982;99(2):237-47.
Shi et al., Three-dimensional electron crystallography of protein microcrystals. Elife. Nov. 19, 2013;2:e01345. doi:10.7554/eLife.01345.

(56) References Cited

OTHER PUBLICATIONS

Shi, A glimpse of structural biology through X-ray crystallography. Cell. Nov. 20, 2014;159(5):995-1014. doi: 10.1016/j.cell.2014.10.051.

Steinhauer et al., DNA origami as a nanoscopic ruler for super-resolution microscopy. Angew Chem Int Ed Engl. 2009;48(47):8870-3. doi: 10.1002/anie.200903308.

Tokunaga et al., Highly inclined thin illumination enables clear single-molecule imaging in cells. Nat Methods. Feb. 2008;5(2):159-61. Epub Jan. 6, 2008.

Tørring et al., DNA origami: a quantum leap for self-assembly of complex structures. Chem Soc Rev. Dec. 2011;40(12):5636-46. doi: 10.1039/c1cs15057j. Epub May 19, 2011.

Tsien, The green fluorescent protein. Annu Rev Biochem. 1998;67:509-44.

Wahlby et al., Sequential immunofluorescence staining and image analysis for detection of large numbers of antigens in individual cell nuclei. Cytometry. Jan. 1, 2002;47(1):32-41.

Wang et al., Prototyping nanorod control: A DNA double helix sheathed within a DNA six-helix bundle. Chem Biol. Aug. 28, 2009;16(8):862-7. doi: 10.1016/j.chembiol.2009.07.008.

Weiss, Fluorescence spectroscopy of single biomolecules. Science. Mar. 12, 1999;283(5408):1676-83.

Wilner et al., Covalently linked DNA nanotubes. Nano Lett. Apr. 14, 2010;10(4):1458-65.

Wlodawer et al., Protein crystallography for aspiring crystallographers or how to avoid pitfalls and traps in macromolecular structure determination. FEBS J. Nov. 2013;280(22):5705-36. doi:10.1111/febs.12495. Epub Sep. 18, 2013.

Xiao et al., Direct determination of haplotypes from single DNA molecules. Nat Methods. Mar. 2009;6(3):199-201. doi:10.1038/nmeth.1301. Epub Feb. 8, 2009.

Xu et al., Multiplexed SNP genotyping using the Qbead system: a quantum dot-encoded microsphere-based assay. Nucleic Acids Res. Apr. 15, 2003;31(8):e43.

Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

Yin et al., Programming biomolecular self-assembly pathways. Nature. Jan. 17, 2008;451(7176):318-22. doi:10.1038/nature06451.

Yin et al., Programming DNA tube circumferences. Science. Aug. 8, 2008;321(5890):824-6. doi:10.1126/science.1157312.

Yurke et al., A DNA-fuelled molecular machine made of DNA. Nature. Aug. 10, 2000;406(6796):605-8.

Zhang et al., Dynamic DNA nanotechnology using strand-displacement reactions. Nat Chem. Feb. 2011;3(2):103-13. doi: 10.1038/nchem.957.

Zhao et al., Advances of multiplex and high throughput biomeolecular detection technologies based on encoding microparticles. Science China Chemistry. 2011;54(8):1185-1201.

Zheng et al., From molecular to macroscopic via the rational design of a self-assembled 3D DNA crystal. Nature. Sep. 3, 2009;461(7260):74-7. doi:10.1038/nature08274.

Ahern, Biochemical, reagents kits offer scientists good return on investment. The Scientist. Jul. 24, 1995;9(15):20. 7 pages. http://www.the-scientist.com/article/print/16618/.

Fedorov et al., Modern methods for modulation and imaging of endogenous microRNA. Bulletin of Almazov Federal Heart, Blood and Endocrinology Center. Oct. 2012;5:77-81.

Lubeck et al., Single-cell systems biology by super-resolution imaging and combinatorial labeling. Nat Methods. Jul. 3, 2012;9(7):743-8. doi:10.1038/nmeth.2069.

Schaus et al, A DNA nanoscope via auto-cycling proximity recording. Nat Commun. Sep. 25, 2017;8(1):696(1-9).

\* cited by examiner

```
                              SEQUENCE LISTING

<160> NUMBER OF SEQ ID NOS: 10

<210> SEQ ID NO 1
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 1
catctaaagc c                                                              11

<210> SEQ ID NO 2
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 2
gaatttcctc g                                                              11

<210> SEQ ID NO 3
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 3
gtttaattgc g                                                              11

<210> SEQ ID NO 4
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 4
acaattcttc g                                                              11

<210> SEQ ID NO 5
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 5
tttcttgctt c                                                              11
```

```
<210> SEQ ID NO 6
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 6
gcattgttac t                                                          11

<210> SEQ ID NO 7
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 7
atatacaagc g                                                          11

<210> SEQ ID NO 8
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 8
gctgtctatt g                                                          11

<210> SEQ ID NO 9
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 9
tctttatgct g                                                          11

<210> SEQ ID NO 10
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 10
caatctcatc c                                                          11
```

HIGH-THROUGHPUT AND HIGHLY MULTIPLEXED IMAGING WITH PROGRAMMABLE NUCLEIC ACID PROBES

RELATED APPLICATIONS

This application is a continuation of U.S. application Ser. No. 15/108,911, filed Jun. 29, 2016, which is a national stage filing under 35 U.S.C. § 371 of international application number PCT/US2015/020034, filed Mar. 11, 2015, which was published under PCT Article 21(2) in English and claims the benefit under 35 U.S.C. § 119(e) of U.S. provisional application Ser. No. 61/951,461, filed Mar. 11, 2014, the entire contents of each of which are incorporated by reference herein.

GOVERNMENT SUPPORT

This invention was made with government support under 1DP2OD007292-01, 5R01EB018659-02, and 1-U01-MH106011-01 awarded by National Institutes of Health; and under N00014-13-1-0593 awarded by U.S. Department of Defense Office of Naval Research; and under CCF-1317291 awarded by National Science Foundation. The government has certain rights in the invention.

FIELD OF THE INVENTION

The invention relates generally to the field of detection and quantification of analytes (e.g., targets).

BACKGROUND OF THE INVENTION

Fluorescence microscopy is a powerful tool for exploring molecules in, for example, a biological system. However, the number of distinct species that can be distinguishably and simultaneously visualized (i.e. the multiplexing power) is limited by the spectral overlap between the fluorophores.

SUMMARY OF THE INVENTION

The present invention provides, inter alia, methods and compositions for detecting, imaging and/or quantitating targets (e.g., biomolecules) of interest. Some of the methods provided herein involve (1) contacting a sample to be analyzed (e.g., a sample suspected of containing one or more targets of interest) with moieties that bind specifically to the targets (each moiety being a binding partner of a given target), wherein each moiety is conjugated to a nucleic acid (referred to herein as a docking strand) and wherein binding partners of different specificity are conjugated to different docking strands, (2) optionally removing unbound binding partners, (3) contacting the sample with labeled (e.g., fluorescently labeled) nucleic acids having a nucleotide sequence that is complementary to and thus specific for one docking strand (such labeled nucleic acids referred to herein as labeled imager strands), (4) optionally removing unbound imager strands, (5) imaging the sample in whole or in part to detect the location and number of bound imager strands, (6) extinguishing signal from the labeled imager strand from the sample (e.g., by bleaching, including photobleaching), and (7) repeating steps (3)-(6) each time with an imager strand having a unique nucleotide sequence relative to all other imager strands used in the method.

Imager strands may be identically labeled, including identically fluorescently labeled. In other embodiments, imager strands having an identical sequence may be identically labeled. The first approach may be more convenient as it requires a single excitation wavelength and detector.

In this manner, it is possible to detect, image and/or quantitate two or more targets in a sample, regardless of their location in the sample, including regardless of whether their location in the sample is so close together to be indistinguishable if signal from the two or more targets was observed simultaneously. Thus, the distance between two or more targets may be below the resolution distance of the imaging system used to detect the targets, and still using the methods provided herein it would be possible to distinguish the two or more targets from each other, thereby facilitating a more accurate and robust detection and quantitation of such targets. In some instances, the resolution distance may be about 50 nm, as an example.

It is to be understood that the "target content" of a sample may be known or suspected, or unknown and unsuspected, prior to performing the method. The binding partners contacting the sample may bind to the sample, or they may not, depending on whether the target is present or absent (e.g., when the target is present, the binding partner may bind to the sample). The imager strands contacting the sample may bind to the sample, or they may not, depending on whether the target is present or absent (e.g., when the target is present, the imager strand may bind a corresponding docking strand bound to the target). "Binding to the sample" means that the binding partner or the imager strand is bound to its respective target or docking strand.

The binding partners may be protein in nature, such as antibodies or antibody fragments. In the context of a binding partner that is an antibody or antibody fragment, the docking strands may be conjugated thereto at a constant region. The binding partner may be an antibody such as a monoclonal antibody, or it may be an antigen-binding antibody fragment such as an antigen-binding fragment from a monoclonal antibody. In some embodiments, the binding partner is a receptor.

The binding partner may be linked to the docking strand through an intermediate linker. In some embodiments, an intermediate linker comprises biotin and/or streptavidin.

The imager strands may be fluorescently labeled (i.e., they are conjugated to a fluorophore). Fluorophores conjugated to imager strands of different nucleotide sequence may be identical to each other, or they may have an emission profile that overlaps or that doesn't overlap with that of other fluorophores. The fluorescently labeled imager strand may comprise at least one fluorophore.

In some instances, fluorescently labeled imager nucleic acids such as imager strands may comprise 1, 2, 3, or more fluorophores.

The sample may be a cell, a population of cells, or a cell lysate from a cell or a population of cells. The target may be a protein.

It will therefore be appreciated that the invention provides a method for detecting analytes by binding analytes to their respective binding partners and sequentially determining the presence of such binding partners, by repeatedly binding, detecting and extinguishing (e.g., bleaching, such as photobleaching) imager strands, that optionally are identically labeled (e.g., identically fluorescently labeled).

Accordingly, the disclosure provides a method comprising (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with labeled imager strands having a nucleotide sequence that is complementary to a docking strand, (4) optionally removing unbound labeled imager strands, (5) imaging the sample to detect location and number of bound labeled imager strands, (6) extinguishing signal from the bound labeled imager strand, and (7) repeating steps (3)-(6), each time with a labeled imager strand having a unique nucleotide sequence relative to all other labeled imager strands.

In some embodiments, the sample is contacted with more than one target-specific binding partner in step (1).

In some embodiments, the target-specific binding partner is an antibody or an antibody fragment.

In some embodiments, the labeled imager strands are labeled identically. In some embodiments, the labeled imager strands each comprise a distinct label. In some embodiments, the labeled imager strands are fluorescently labeled imager strands.

In some embodiments, the one or more targets are proteins. In some embodiments, the sample is a cell, a cell lysate or a tissue lysate.

In some embodiments, the sample is imaged in step (5) using confocal or epi-fluorescence microscopy.

In some embodiments, extinguishing signal in step (6) comprises photobleaching.

The disclosure further provides a composition comprising a sample bound to more than one target-recognition moieties such as target-specific binding partners, each target-recognition moiety bound to a docking nucleic acid such as a docking strand, and at least one docking nucleic acid stably bound to a labeled imager nucleic acid such as an imager strand.

The disclosure further provides a composition comprising a sample bound to more than one target-specific binding partners, each binding partner bound to a docking strand, and at least one docking strand stably bound to a labeled imager strand.

The disclosure further provides a method comprising (1) contacting a sample being tested for the presence of one or more targets with one or more target-recognition moieties such as target-specific binding partners, wherein each target-recognition moiety is linked to a docking nucleic acid such as a docking strand, and wherein target-recognition moieties of different specificity are linked to different docking nucleic acids, (2) optionally removing unbound target-recognition moieties, (3) contacting the sample with labeled imager nucleic acids such as imager strands having a nucleotide sequence that is complementary to a docking nucleic acid, (4) optionally removing unbound labeled imager nucleic acids, (5) imaging the sample to detect location and number of bound labeled imager nucleic acids, (6) removing the bound labeled imager nucleic acids from the docking nucleic acids by altering temperature and/or buffer condition, and (7) repeating steps (3)-(6), each time with a labeled imager nucleic acid having a unique nucleotide sequence relative to all other labeled imager nucleic acids. The imager nucleic acid dissociates from the docking nucleic acid spontaneously under such conditions.

The disclosure further provides a method comprising (1) contacting a sample being tested for the presence of one or more targets with one or more target-specific binding partners, wherein each target-specific binding partner is linked to a docking nucleic acid, and wherein target-specific binding partners of different specificity are linked to different docking nucleic acids, (2) optionally removing unbound target-specific binding partners, (3) contacting the sample with labeled imager nucleic acids having a nucleotide sequence that is complementary to a docking nucleic acid, (4) optionally removing unbound labeled imager nucleic acids, (5) imaging the sample to detect location and number of bound labeled imager nucleic acids, (6) removing the bound labeled imager nucleic acids from the docking nucleic acids by altering temperature and/or buffer condition, and (7) repeating steps (3)-(6), each time with a labeled imager nucleic acid having a unique nucleotide sequence relative to all other labeled imager nucleic acids. The imager nucleic acid dissociates from the docking nucleic acid spontaneously under such conditions.

In some embodiments, the labeled imager nucleic acids are removed from the docking nucleic acids by decreasing salt concentration, addition of a denaturant, or increasing temperature. In some embodiments, the salt is Mg++. In some embodiments, the denaturant is formamide, urea or DMSO.

The disclosure further provides a method comprising (1) contacting a sample being tested for the presence of one or more targets with one or more target-recognition moieties such as target-specific binding partners, wherein each target-recognition moiety is linked to a docking nucleic acid such as a docking strand, and wherein target-recognition moieties of different specificity are linked to different docking nucleic acids, (2) optionally removing unbound target-recognition moieties, (3) contacting the sample with labeled imager nucleic acids such as imager strands having a nucleotide sequence that is complementary to a docking nucleic acid, (4) optionally removing unbound labeled imager nucleic acids, (5) imaging the sample to detect location and number of bound labeled imager nucleic acids, (6) removing the bound labeled imager nucleic acids from the docking nucleic acids, and (7) repeating steps (3)-(6), each time with a labeled imager nucleic acid having a unique nucleotide sequence relative to all other labeled imager nucleic acids.

The disclosure further provides a method comprising (1) contacting a sample being tested for the presence of one or more targets with one or more target-specific binding partners, wherein each target-specific binding partner is linked to a docking nucleic acid, and wherein target-specific binding partners of different specificity are linked to different docking nucleic acids, (2) optionally removing unbound target-specific binding partners, (3) contacting the sample with labeled imager nucleic acids having a nucleotide sequence that is complementary to a docking nucleic acid, (4) optionally removing unbound labeled imager nucleic acids, (5) imaging the sample to detect location and number of bound labeled imager nucleic acids, (6) removing the bound labeled imager nucleic acids from the docking nucleic acids, and (7) repeating steps (3)-(6), each time with a labeled imager nucleic acid having a unique nucleotide sequence relative to all other labeled imager nucleic acids.

In some embodiments, in step (6) the labeled imager nucleic acids are not removed from the docking nucleic acids by strand displacement in the presence of a competing nucleic acid.

In some embodiments, in step (6) the labeled imager nucleic acids are removed from the docking nucleic acids by chemically, photochemically, or enzymatically cleaving, modifying or degrading the labeled imager nucleic acids.

In some embodiments, when the labeled imager nucleic acid is bound to its respective docking nucleic acid, there is no single-stranded region on the imager nucleic acid or the docking nucleic acid. In some embodiments, the docking nucleic acid does not have a toehold sequence. In some embodiments, the imager nucleic acid does not have a toehold sequence.

In some embodiments, the labeled imager nucleic acid is not self-quenching.

The disclosure further provides a method comprising (1) contacting a sample being tested for the presence of one or more targets with one or more target-recognition moieties such as target-specific binding partners, wherein each target-recognition moiety is linked to a docking nucleic acid such as a docking strand, and wherein target-recognition moieties of different specificity are linked to different docking nucleic acids, (2) optionally removing unbound target-recognition moieties, (3) contacting the sample with labeled imager nucleic acids such as imager strands having a nucleotide sequence that is complementary to a docking nucleic acid, (4) optionally removing unbound labeled imager nucleic acids, (5) imaging the sample to detect location and number of bound labeled imager nucleic acids, (6) inactivating the bound labeled imager nucleic acids, by removing or modifying their signal-emitting moieties without removing the imager nucleic acid in its entirety, and (7) repeating steps (3)-(6), each time with a labeled imager nucleic acids having a unique nucleotide sequence relative to all other labeled imager nucleic acids.

The disclosure further provides a method comprising (1) contacting a sample being tested for the presence of one or more targets with one or more target-specific binding partners, wherein each target-specific binding partner is linked to a docking nucleic acid, and wherein target-specific binding partners of different specificity are linked to different docking nucleic acids, (2) optionally removing unbound target-specific binding partners, (3) contacting the sample with labeled imager nucleic acids having a nucleotide sequence that is complementary to a docking nucleic acid, (4) optionally removing unbound labeled imager nucleic acids, (5) imaging the sample to detect location and number of bound labeled imager nucleic acids, (6) inactivating the bound labeled imager nucleic acids, by removing or modifying their signal-emitting moieties without removing the imager nucleic acid in its entirety, and (7) repeating steps (3)-(6), each time with a labeled imager nucleic acids having a unique nucleotide sequence relative to all other labeled imager nucleic acids.

Various embodiments apply equally to the afore-mentioned methods. These embodiments are as follows:

In some embodiments, the sample is contacted with more than one target-specific binding partner in step (1). In some embodiments, the target-specific binding partner is an antibody or an antibody fragment. In some embodiments, the target-specific binding partner is a natural or engineered ligand, a small molecule, an aptamer, a peptide or an oligonucleotide.

In some embodiments, the labeled imager nucleic acids are labeled identically. In some embodiments, the labeled imager nucleic acids each comprise a distinct label. In some embodiments, the labeled imager nucleic acids are fluorescently labeled imager nucleic acids.

In some embodiments, the one or more targets are proteins. In some embodiments, the sample is a cell, a cell lysate or a tissue lysate.

In some embodiments, the sample is imaged in step (5) using confocal or epi-fluorescence microscopy.

In some embodiments, the unbound docking nucleic acid is partially double-stranded. In some embodiments, the unbound imager nucleic acid is partially double-stranded.

In some embodiments, the imager nucleic acid is a molecular beacon or comprises a hairpin secondary structure. In some embodiments, the imager nucleic acid is a molecular beacon or comprises a hairpin secondary structure that is self-quenching. In some embodiments, the imager nucleic acid is a hemiduplex. In some embodiments, the hemiduplex is self-quenching. In some embodiments, the imager nucleic acid is bound to multiple signal-emitting moieties through a dendrimeric structure or a polymeric structure. The imager nucleic acid may be linear or branched.

In some embodiments, the docking nucleic acid comprises a hairpin secondary structure.

These and other embodiments will be described in greater detail herein.

```
Sequence a1:
                               (SEQ ID NO: 1)
5'-CATCTAAAGCC-3';

Sequence a2:
                               (SEQ ID NO: 2)
5'-GAATTTCCTCG-3';

Sequence a3:
                               (SEQ ID NO: 3)
5'-GTTTAATTGCG-3';

Sequence a4:
                               (SEQ ID NO: 4)
5'-ACAATTCTTCG-3';

Sequence a5:
                               (SEQ ID NO: 5)
5'-TTTCTTGCTTC-3';

Sequence a6:
                               (SEQ ID NO: 6)
5'-GCATTGTTACT-3';
```

-continued

Sequence a7:
(SEQ ID NO: 7)
5'-ATATACAAGCG-3';

Sequence a8:
(SEQ ID NO: 8)
5'-GCTGTCTATTG-3';

Sequence a9:
(SEQ ID NO: 9)
5'-TCTTTATGCTG-3';

Sequence a10:
(SEQ ID NO: 10)
5'-CAATCTCATCC-3'.

DESCRIPTION OF THE INVENTION

The invention provides, inter alia, compositions and methods for multiplexed fluorescence imaging, for example, in a cellular environment using nucleic acid-based imaging probes (e.g., DNA-based imaging probes). Methods provided herein are based, in part, on the programmability of nucleic acid docking strands and imager strands. That is, for example, docking strands and imager strands can be designed such that they bind to each other under certain conditions for a certain period of time. This programmability permits stable binding of imager strands to docking strands, as provided herein. Generally, the methods provided herein are directed to identifying one or more target(s) (e.g., biomolecule(s) such as a protein or nucleic acid) in a particular sample (e.g., biological sample). In some instances, whether or not one or more target(s) is present in sample is unknown. Thus, methods of the present disclosure may be used to determine the presence or absence of one or more target(s) in a sample suspected of containing the target(s). In any one of the aspects and embodiments provided herein, a sample may contain or may be suspected of containing one or more target(s).

Figure 1:
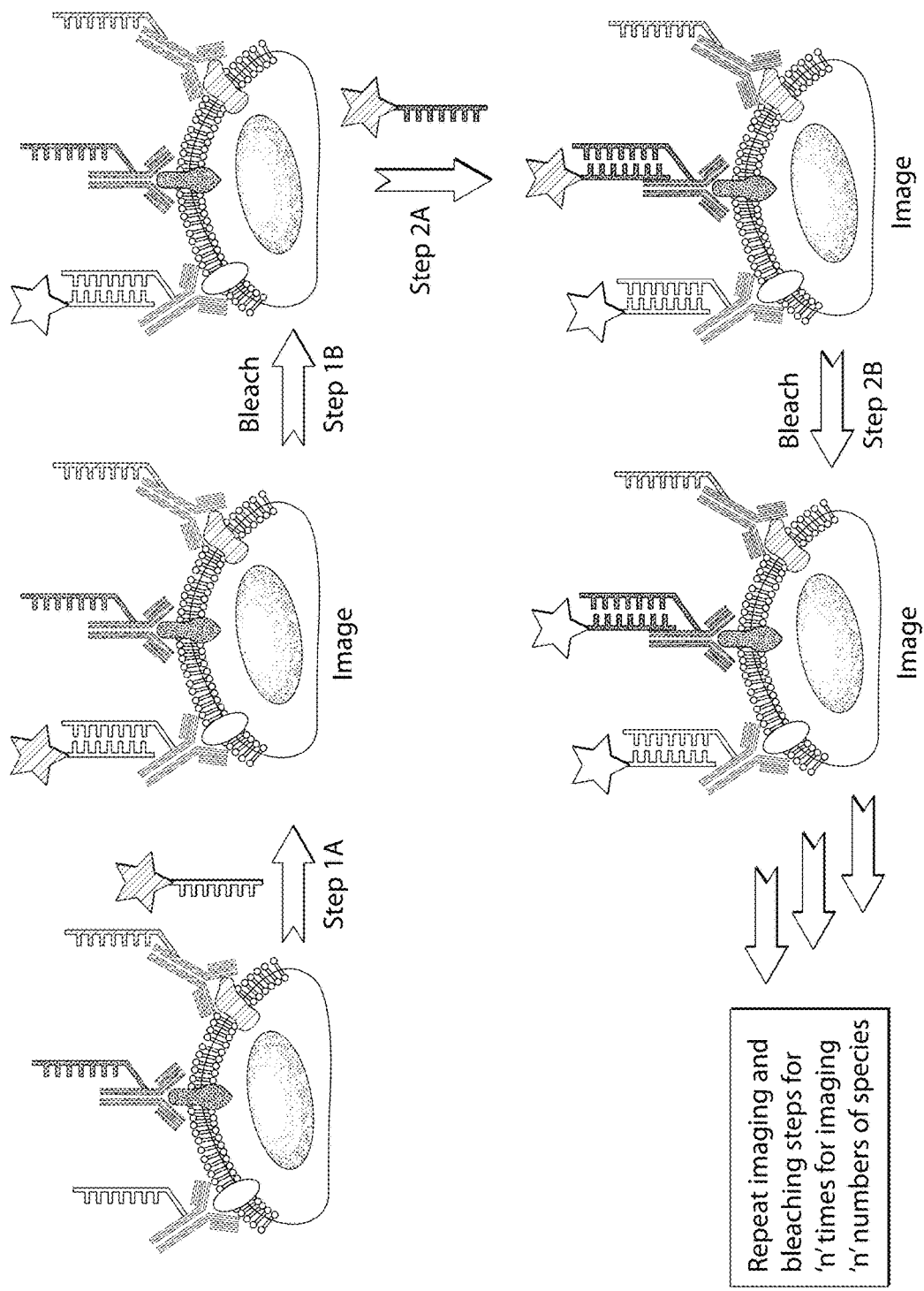
FIG. 1 is a schematic of one embodiment of a high-throughput and intrinsically scalable multiplexed imaging approach provided in this disclosure. Cells are imaged after probe hybridization and then photobleached before a subsequent round of imaging.

Thus, the invention provides methods for performing high-throughput and highly multiplexed imaging and analyte/target detection based on programmable nucleic acid (e.g., DNA) probes. These methods rely on a sequential imaging approach employing orthogonal imager strands that can stably attach to a complementary docking strand immobilized on binding partners, such as antibodies (FIG. 1). After hybridization and imaging with an imager strand, an extinguishing step (such as a photobleaching step) is performed to eliminate and/or reduce fluorescence from the hybridized (bound) imager strands.

Figure 2:
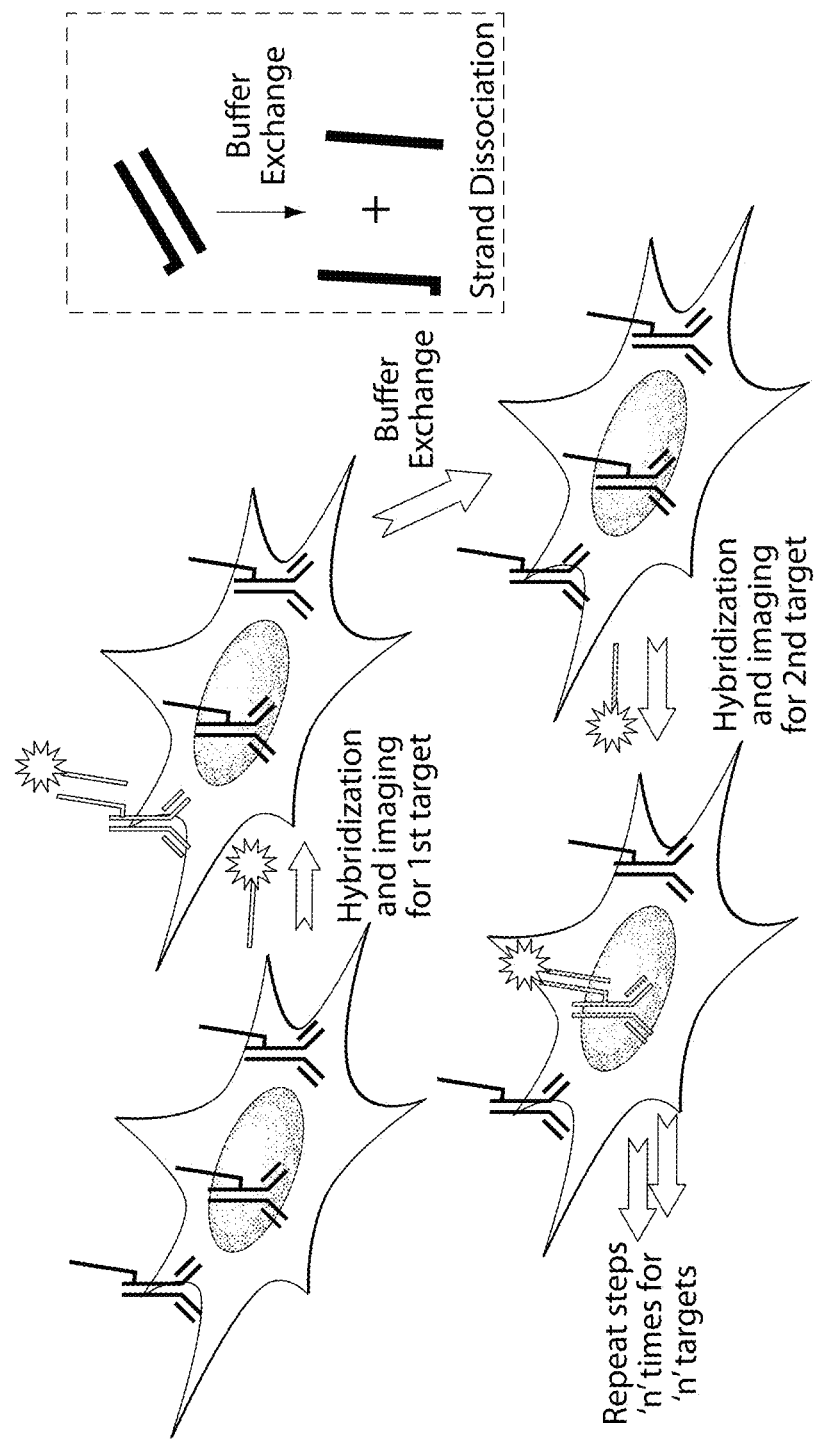
FIG. 2 is a schematic of one embodiment of a high-throughput and intrinsically scalable multiplexed imaging approach based on buffer exchange using solutions with slight denaturation characteristics, such as decreased salt concentration, increased formamide concentration, or higher temperature.

In another embodiment, the methods utilize weaker binding between docking and imaging strands in order to remove signal. For example, the hybridization conditions may be changed such that the melting point of the duplex that is formed between the docking or imager strands is slightly above room temperature (e.g., 25° C.) or the imaging temperature. The labeling step (i.e., the step at which the imager strands are bound to their respective docking strands) and the imaging step are performed as described above. As an example, after the first target is imaged, the sample is subjected to a denaturing condition. The denaturing condition may be provided in a buffer exchange step using a solution with for example lower salt concentration, presence of or increase in the concentration of a denaturant such as formamide, or increased temperature (FIG. 2). The sample may be alternatively or additionally exposed to an increased temperature. The aforementioned increases or decreases are relative to the conditions existing at the labeling step (i.e., when the imager strand is bound to the docking strand). In the case of the buffer exchange, the sample may be washed, the buffer exchange may be repeated, the sample may be washed again, and then the next imager strand may be added to the sample.

For multiplexing, different reservoirs of orthogonal imager strands are sequentially applied after every step of, for example, photobleaching or other method for extinguishing signal or imager strand inactivation or removal to the same sample in order to potentially image an infinite number of targets. Unlike traditional imaging approaches, where multiplexing is limited by spectral overlap between color channels, the methods provided herein are only limited by the number of possible orthogonal nucleotide sequences (of the docking strands or alternatively the imager strands). As a larger number of orthogonal nucleotide sequences can be readily designed, this approach has intrinsically scalable multiplexing capability just by using a single fluorophore. This method can be readily integrated with standard microscopy setups (e.g., confocal or epi-fluorescence microscopes), allowing high throughput analysis of the sample.

The methods have applicability in, for example, high-throughput screening assays such as drug screening assays. This imaging approach allows analysis of large populations of cells (~1,000-10,000) or tissue samples in an ultra-multiplexed format while imaging using standard confocal or epi-fluorescence microscope. Screening large numbers of targets such as proteins from the same sample in a high-throughput manner will provide information about new drugs or modifiers while providing cellular heterogeneity information. The large scale screening of tissue samples with high-throughput and ultra-multiplexed imaging capabilities will be useful in pathology analysis, for example, in a hospital or other service provider setting.

Methods provided herein can also be used to identify the absolute quantity of a single target (e.g., such as, for example, a particular protein), or the quantity of a single target relative to one or more other targets.

Further, methods provided herein may be used to identify the location of a target within a sample or relative to other targets in the sample.

This disclosure therefore provides a method comprising (1) contacting a sample simultaneously with a plurality of sequence-labeled target-recognition moieties, (2) introducing imager nucleic acids such as imager strands recognizing, through sequence complementarity, a subset of docking nucleic acids such as docking strands in the sequence-labeled target-recognition moieties, (3) removing or inactivating the imager nucleic acids or extinguishing signal from the imager nucleic acids, and (4) repeating step (2) and optionally step (3) at least once in order to image and detect one or more additional docking nucleic acids.

The method may optionally comprise labeling a plurality of target-recognition moieties with docking nucleic acids such as docking strands to form sequence-labeled target-recognition moieties.

This disclosure further provides a method comprising (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with labeled imager strands having a nucleotide sequence that is complementary to a docking strand, (4) optionally removing unbound labeled imager strands, (5) imaging the sample to detect location and number of bound labeled imager strands, (6) extinguishing signal from the bound labeled imager strand, and (7) repeating steps (3)-(6), each time with a labeled imager strand having a unique nucleotide sequence relative to all other labeled imager strands.

Steps (3)-(6) may be repeated once or multiple times. For example, steps (3)-(6) may be repeated 1-10 times or more. In some embodiments, steps (3)-(6) are repeated 1, 2, 3, 4, 5, 6, 7, 8, 9 or 10 times.

This disclosure further provides a method comprising (1) contacting a sample being tested for the presence of one or more targets with one or more target-recognition moieties such as target-specific binding partners, wherein each target-recognition moiety is linked to a docking nucleic acid, and wherein target-recognition moieties of different specificity are linked to different docking nucleic acids, (2) optionally removing unbound target-recognition moieties, (3) contacting the sample with labeled imager nucleic acids such as imager strands having a nucleotide sequence that is complementary to a docking nucleic acid, (4) optionally removing unbound labeled imager nucleic acids, (5) imaging the sample to detect location and number of bound labeled imager nucleic acids, (6) removing the bound labeled imager nucleic acids from the docking nucleic acids, and (7) repeating steps (3)-(6), each time with a labeled imager nucleic acid having a unique nucleotide sequence relative to all other labeled imager nucleic acids.

Steps (3)-(6) may be repeated once or multiple times. For example, steps (3)-(6) may be repeated 1-10 times or more. In some embodiments, steps (3)-(6) are repeated 1, 2, 3, 4, 5, 6, 7, 8, 9 or 10 times.

This disclosure further provides a method comprising (1) contacting a sample being tested for the presence of one or more targets with one or more target-recognition moieties such as target-specific binding partners, wherein each target-recognition moieties is linked to a docking nucleic acid such as a docking strand, and wherein target-recognition moieties of different specificity are linked to different docking nucleic acids, (2) optionally removing unbound target-recognition moieties, (3) contacting the sample with labeled imager nucleic acids such as imager strands having a nucleotide sequence that is complementary to a docking nucleic acid, (4) optionally removing unbound labeled imager nucleic acids, (5) imaging the sample to detect location and number of bound labeled imager nucleic acids, (6) inactivating the bound labeled imager nucleic acids, by removing or modifying their signal-emitting moieties without removing the imager nucleic acid in its entirety, and (7) repeating steps (3)-(6), each time with a labeled imager nucleic acid having a unique nucleotide sequence relative to all other labeled imager nucleic acids.

Steps (3)-(6) may be repeated once or multiple times. For example, steps (3)-(6) may be repeated 1-10 times or more. In some embodiments, steps (3)-(6) are repeated 1, 2, 3, 4, 5, 6, 7, 8, 9 or 10 times.

In some embodiments, the methods provided herein include a step of removing an imager nucleic acid such as an imager strand that is bound to a docking nucleic acids such as a docking strand, using a method other than strand displacement.

In some embodiments, the methods provided herein include a step of removing an imager nucleic acid such as an imager strand that is bound to a docking nucleic acid such as a docking strand, wherein the imager nucleic acid emits signal (i.e., such signal is not quenched) prior to binding to the docking nucleic acid.

In some embodiments, the methods provided herein include a step of removing an imager nucleic acid such as an imager strand that is bound to a docking nucleic acid such as a docking strand, wherein the imager nucleic acid is removed using a nucleic acid that does not comprise a quencher.

In each of the foregoing methods, the docking nucleic acid including the docking strand may be a single-stranded docking nucleic acid or docking strand, or it may be a double-stranded docking nucleic acid or docking strand, or it may be a partially double-stranded docking nucleic acid or docking strand (e.g., containing a single-stranded and a double-stranded region).

In some embodiments, where a plurality of target-recognition moieties, including a plurality of binding partners, are used, the plurality may be contacted with the sample, and thus with targets of interest, simultaneously. The target-recognition moieties such as the binding partners need not be contacted with the sample sequentially, although they can be.

These various methods facilitate high throughput imaging with spinning disk confocal microscopy. It is estimated that a one color whole cell 3D imaging process would take on average about 30 seconds. The method allows for imaging of large areas (e.g., up to mm scale) with compatible 10× or 20× objective. An imaging depth of about 30-50 microns may be achieved. The methods provided herein have been used to stain actin, Ki-67, clathrin, cytokeratin, among others (data not shown).

Binding Partners

The methods employ binding partners conjugated to nucleic acids (e.g., docking nucleic acids such as docking strands). These may be referred to herein as binding partner-nucleic acid conjugates ("BP-NA conjugates"). They may also be referred to as sequence-labeled target-recognition moieties. As used herein, "binding partner-nucleic acid conjugate," or "BP-NA conjugate," refers to a molecule linked (e.g., through an N-Hydroxysuccinimide (NHS) linker) to a single-stranded nucleic acid (e.g., DNA) docking strand.

The binding partner of the conjugate may be any moiety (e.g., antibody or aptamer) that has an affinity for (e.g., binds to) a target, such as a biomolecule (e.g., protein or nucleic acid), of interest. In some embodiments, the binding partner is a protein. BP-NA-conjugates that comprise a protein (or peptide) linked to a docking strand may be referred to herein as "protein-nucleic acid conjugates," or "protein-NA conjugates." Examples of proteins for use in the conjugates of the invention include, without limitation, antibodies (e.g., monoclonal antibodies), antigen-binding antibody fragments (e.g., Fab fragments), receptors, peptides and peptide aptamers. Other binding partners may be used in accordance with the invention. For example, binding partners that bind to targets through electrostatic (e.g., electrostatic particles), hydrophobic or magnetic (e.g., magnetic particles) interactions are contemplated herein.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_H$ and $V_L$ domains of a single arm of an antibody, (v) a dAb fragment (Ward et al., Nature 341:544 546, 1989), which consists of a $V_H$ domain; and (vi) an isolated complementarity determining region (CDR) or (vii) a combination of two or more isolated CDRs, which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see, e.g., Bird et al. Science 242:423 426, 1988; and Huston et al. Proc. Natl. Acad. Sci. USA 85:5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

As used herein, "receptors" refer to cellular-derived molecules (e.g., proteins) that bind to ligands such as, for example, peptides or small molecules (e.g., low molecular weight (<900 Daltons) organic or inorganic compounds).

As used herein, "peptide aptamer" refers to a molecule with a variable peptide sequence inserted into a constant scaffold protein (see, e.g., Baines I C, et al. Drug Discov. Today 11:334-341, 2006).

In some embodiments, the molecule of the BP-NA conjugate is a nucleic acid such as, for example, a nucleic acid aptamer. As used herein, "nucleic acid aptamer" refers to a small RNA or DNA molecules that can form secondary and tertiary structures capable of specifically binding proteins or other cellular targets (see, e.g., Ni X, et al. Curr Med Chem. 18(27): 4206-4214, 2011). Thus, in some embodiments, the BP-NA conjugate may be an aptamer-nucleic acid conjugate.

Some embodiments of the invention use target-recognition moieties to identify and label targets. Target-recognition moieties are agents that specifically recognize targets of interest in the sample. Examples of target-recognition moieties include binding partners such as those recited herein. Target-recognition moieties include antibodies, antibody fragments and antibody derivatives such as single-chain antibodies, single-chain Fv domains, Fab domains, nanobodies, and the like, peptides, aptamers, and oligonucleotides (e.g., to detect nucleic acids of interest in procedures such as fluorescence in situ hybridization, or FISH).

Docking Nucleic Acids such as Docking Strands

Figure 7:
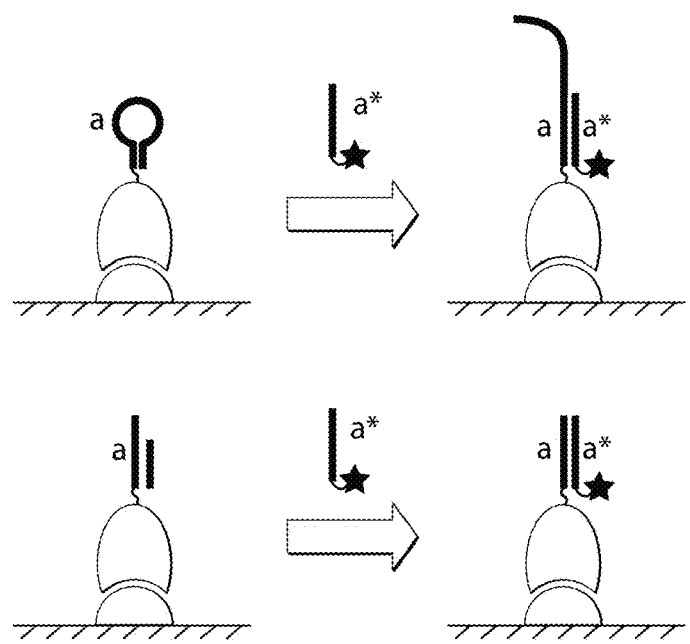
FIG. 7 is a schematic of one embodiment of a non-single-stranded docking strand.

Certain embodiments of the invention may refer to docking nucleic acids. Docking nucleic acids include docking strands as described herein. Docking nucleic acids are linear nucleic acids capable of binding to a nucleic acid having a complementary sequence (such as an imager nucleic acid). A docking nucleic acid may be comprised of or may consist of DNA, RNA, or nucleic acid-like structures with other phosphate-sugar backbones (e.g. 2'-O-methyl RNA, 2'-fluoral RNA, LNA, XNA) or backbones comprising non-phosphate-sugar moieties (e.g., peptide nucleic acid and morpholino). The nucleobases may include naturally occurring nucleobases such as adenine, thymine, guanine, cytosine, inosine, and their derivatives, as well as non-naturally occurring nucleobases such as isoC, isoG, dP and dZ. A docking nucleic acid, when not bound to its complementary imager nucleic acid, may be single-stranded without stable secondary structure. Alternatively, the docking nucleic acid may comprise secondary structure such as a hairpin loop (FIG. 7, top). A docking nucleic acid may be part of a multi-strand complex (FIG. 7, bottom).

As used herein, a "docking strand" refers to a single-stranded nucleic acid (e.g., DNA) capable of stably binding to its complementary imager strands. Stable binding may be a result of the length of the docking strand (and conversely the imager strand) or it may be the result of the particular conditions under which hybridization occurs (e.g., salt concentration, temperature, etc.). In some embodiments, a docking strand is about 20 to about 60, or more, nucleotides in length. A docking strand may be capable of binding to one or more identical imager strands (of identical sequence and identically labeled).

Imager Nucleic Acids such as Imager Strands

Figure 8:
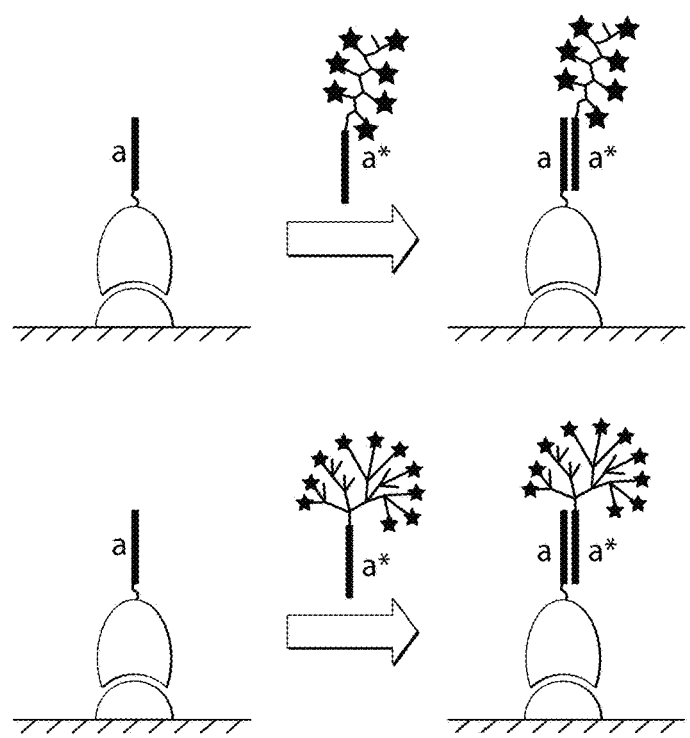
FIG. 8 is a schematic of one embodiment of an imager strand that recruits multiple copies of the signal-emitting moieties to the docking strand.

Certain embodiments of the invention may refer to imager nucleic acids. Imager nucleic acids include imager strands as described herein. Imager nucleic acids are nucleic acids that can (1) interact with a docking nucleic acid via sequence-specific complementarity and (2) recruit a signal-emitting moiety or multiple copies of signal-emitting moieties by covalent or non-covalent interactions. The imager nucleic acids may be linear or branched as described herein. One imager nucleic acid may recruit multiple copies of the signal-emitting moiety via a polymeric (FIG. 8, top) or dendrimeric structure (FIG. 8, bottom). For example, a polymeric or dendrimeric structure can be synthesized chemically using methods such as those discussed in Nazemi A. et al. Chemistry of Bioconjugates: Synthesis, Characterization, and Biomedical Applications, Published Online: 13 Feb. 2014) and references provided therein. Alternatively, the polymeric or dendrimeric structure can be formed by DNA hybridization as shown, for example, in Dirks R. et al. Proc. Nat. Acad. Sci. U.S.A., 2004; 1010(43): 15275-78; and in Um S. H. et al. Nat. Protocols 2006; 1:995-1000, each of which is incorporated by reference herein.

An imager nucleic acid may be comprised of or may consist of DNA, RNA, or nucleic acid-like structures with other phosphate-sugar backbones (e.g. 2'-O-methyl RNA, 2'-fluoral RNA, LNA, XNA) or backbones comprising non-phosphate-sugar moieties (e.g., peptide nucleic acid and morpholino). The nucleobases may include naturally occurring nucleobases such as adenine, thymine, guanine, cytosine, inosine, and their derivatives, as well as non-naturally occurring nucleobases such as isoC, isoG, dP and dZ.

In some embodiments, an imager nucleic acid is about 30 to about 60 nucleotides, or more, in length, including 30, 35, 40, 45, 50, 55 or 60 nucleotides in length. In some embodiments, an imager nucleic acid is 30 to 40, 30 to 50, 40 to 50, 40 to 60, or 50 to 60 nucleotides in length.

Figure 9:
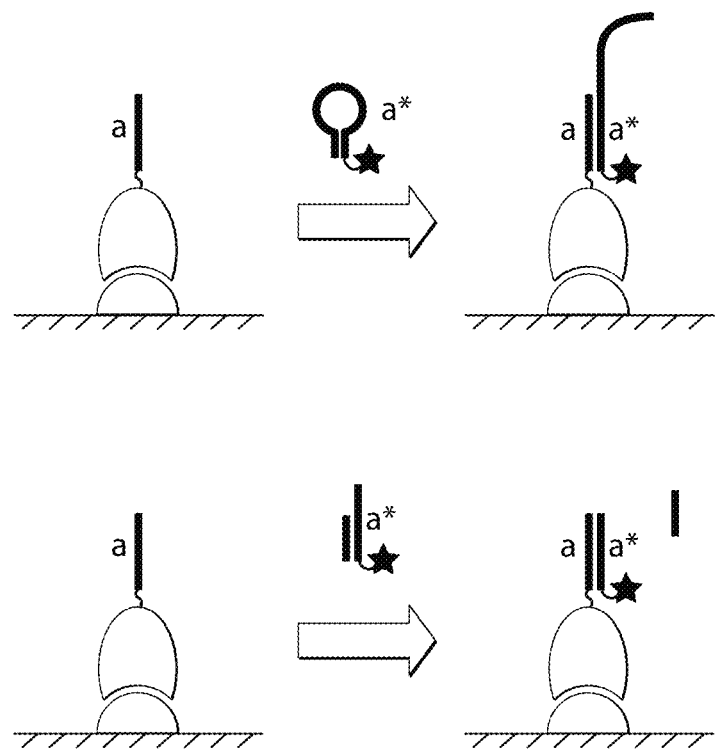
FIG. 9 is a schematic of one embodiment of a non-single-stranded imager strand.

An imager nucleic acid, when not bound to its complementary docking nucleic acid, may be single-stranded without stable secondary structure. Alternatively, the imager nucleic acid may comprise secondary structure such as a hairpin loop (FIG. 9, top). An imager nucleic acid may be part of a multi-strand complex (FIG. 9, bottom).

Figure 5:
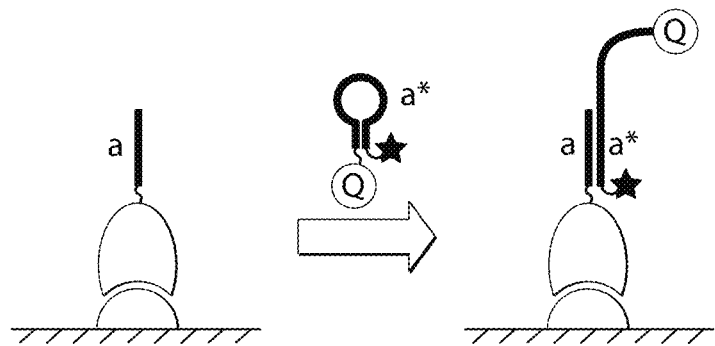
FIG. 5 is a schematic of one embodiment of a molecular beacon-like self-quenching imager strand.
Figure 6:
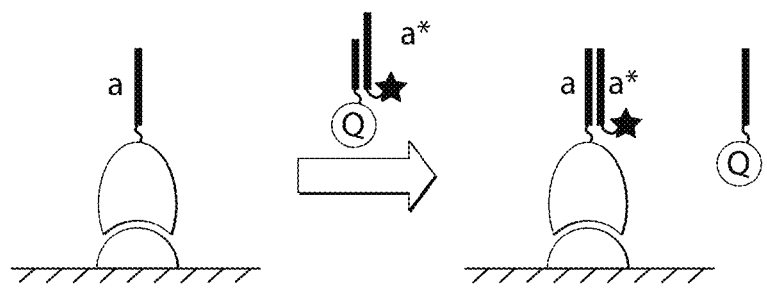
FIG. 6 is a schematic of one embodiment of a hemiduplex self-quenching imager strand.

In some embodiments, the imager strand can be self-quenching, intending that the unbound imager nucleic acid may carry a quencher moiety that is in close proximity with the signal-emitting moiety such as a fluorophore. To achieve this, the imager nucleic acid can be designed to adopt either a molecular beacon-like structure (FIG. 5) or a hemiduplex structure (FIG. 6).

This self-quenching variation can be used to reduce background and/or avoid the washing step. Additionally or alternatively, the binding and imaging buffer may contain additives routinely used in FISH, Northern Blotting and Southern Blotting (e.g., negatively charged polymers such as dextran sulfate and heparin) to reduce non-specific binding.

A "signal-emitting moiety," as used herein, is a moiety that, under certain conditions, emits detectable signal, such as photon, radiation, positron, electromagnetic wave, and magnetic-nuclear resonance.

As used herein, an "imager strand" is a single-stranded nucleic acid (e.g., DNA) that is about 30 to about 60 nucleotides, or more, in length. An imager strand of the invention is complementary to a docking strand and stably binds to the docking strand. Stable binding intends that the imager and docking strands remained bound to each other for the length of the assay, or for at least 30 minutes, or for at least for 60 minutes, or for at least for 2 hours, or more. Such binding may or may not be reversible or irreversible.

In some embodiments, a docking nucleic acid is considered stably bound to an imager nucleic acid such as an imager strand if the nucleic acids remain bound to each other for (or for at least) 30, 35, 40, 45, 50, 55 or 60 minutes (min). In some embodiments, a docking nucleic acid is considered stably bound to an imager nucleic acid if the nucleic acids remain bound to each other for (or for at least) 30 to 60 min, 30 to 120 min, 40 to 60 min, 40 to 120 min, or 60 to 120 min. Such binding may or may not be reversible, or may or may not be irreversible.

As used herein, "binding" refers to an association between at least two molecules due to, for example, electrostatic, hydrophobic, ionic and/or hydrogen-bond interactions, optionally under physiological conditions.

Two nucleic acids, or nucleic acid domains, are "complementary" to one another if they base-pair, or bind, with each other to form a double-stranded nucleic acid molecule via Watson-Crick interactions.

In some embodiments, nucleic acids of the invention such as the docking nucleic acids and the imager nucleic acids bind to each other with "perfect complementary," which refers to 100% complementary (e.g., 5'-ATTCGC-3' is perfectly complementary to 5' GCGAAT-3').

Imager strands of the invention may be labeled with a detectable label (e.g., a fluorescent label, and thus are considered "fluorescently labeled"). For example, in some embodiments, an imager strand may comprise at least one (i.e., one or more) fluorophore. Examples of fluorophores for use in accordance with the invention include, without limitation, xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin).

Imager nucleic acids including imager strands may be covalently labeled with a detectable label such as those recited herein or known in the art. In some instances, imager nucleic acids including imager strands may comprise 2, 3, 4, or more detectable labels such as fluorophores.

Orthogonal imager nucleic acids including imager strands may comprise a distinct label (e.g., a red fluorophore, a blue fluorophore, or a green fluorophore), or they may all comprise the same label (e.g., red fluorophores) even if they differ in nucleotide sequence.

Sequence-Labeled Target Recognition Moieties such as Binding Partner and Docking Strand Conjugates The BP-NA conjugates (e.g., protein-nucleic acid conjugates) of the invention may, in some embodiments, comprise an intermediate linker that links (e.g., covalently or non-covalently) the binding partner to a docking strand. The intermediate linker may comprise biotin and/or streptavidin. For example, in some embodiments, an antibody and a docking strand may each be biotinylated (i.e., linked to at least one biotin molecule) and linked to each other through biotin binding to an intermediate streptavidin molecule. Other intermediate linkers may be used in accordance with the invention. In some embodiments, such as those where the molecule is a nucleic acid, an intermediate linker may not be required. For example, the docking strand of a BP-NA conjugate may be an extension (e.g., 5' or 3' extension) of a nucleic acid molecule such as, for example, a nucleic acid aptamer. Similar approaches may be used to generate sequence-labeled target recognition moieties as provided herein.

Pluralities of BP-NA conjugates (e.g., protein-nucleic acid conjugates) and imager strands are provided herein. A plurality may be a population of the same species or distinct species. A plurality of BP-NA conjugates of the same species may comprise conjugates that all bind to the same target (e.g., biomolecule) (e.g., the same epitope or region/domain). Conversely, a plurality of BP-NA conjugates of distinct species may comprise conjugates, or subsets of conjugates, each conjugate or subset of conjugates binding to a distinct epitope on the same target or to a distinct target. A plurality of imager strands of the same species may comprise imager strands with the same nucleotide sequence and the same fluorescent label (e.g., Cy2, Cy3 or Cy4). Conversely, a plurality of imager strands of distinct species may comprise imager strands with distinct nucleotide sequences (e.g., DNA sequences) and distinct fluorescent labels (e.g., Cy2, Cy3 or Cy4) or with distinct nucleotide sequences and the same fluorescent (e.g., all Cy2). The number of distinct species in a given plurality of BP-NA conjugates is limited by the number of binding partners (e.g., antibodies) and the number of docking strands of different nucleotide sequence (and thus complementary imager strands). In some embodiments, a plurality of BP-NA conjugates (e.g., protein-nucleic acid conjugates) comprises at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ BP-NA conjugates. Likewise, in some embodiments, a plurality of fluorescently labeled imager strands comprises at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ fluorescently labeled imager strands. In some embodiments, a plurality may contain 1 to about 200 or more distinct species of BP-NA conjugates and/or imager strands. For example, a plurality may contain at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200 or more distinct species. In some embodiments, a plurality may contain less than about 5 to about 200 distinct species of BP-NA conjugates and/or imager strands. For example, a plurality may contain less than 5, 6, 7, 8, 9, 10, 15, 20, 25, 30, 35, 40, 45, 50, 55, 60, 65, 70, 75, 80, 85, 90, 95, 100, 125, 150, 175 or 200 distinct species. These embodiments apply to sequence-labeled target recognition moieties as provided herein.

Signal or Imager Nucleic Acid Inactivation

Figure 3:
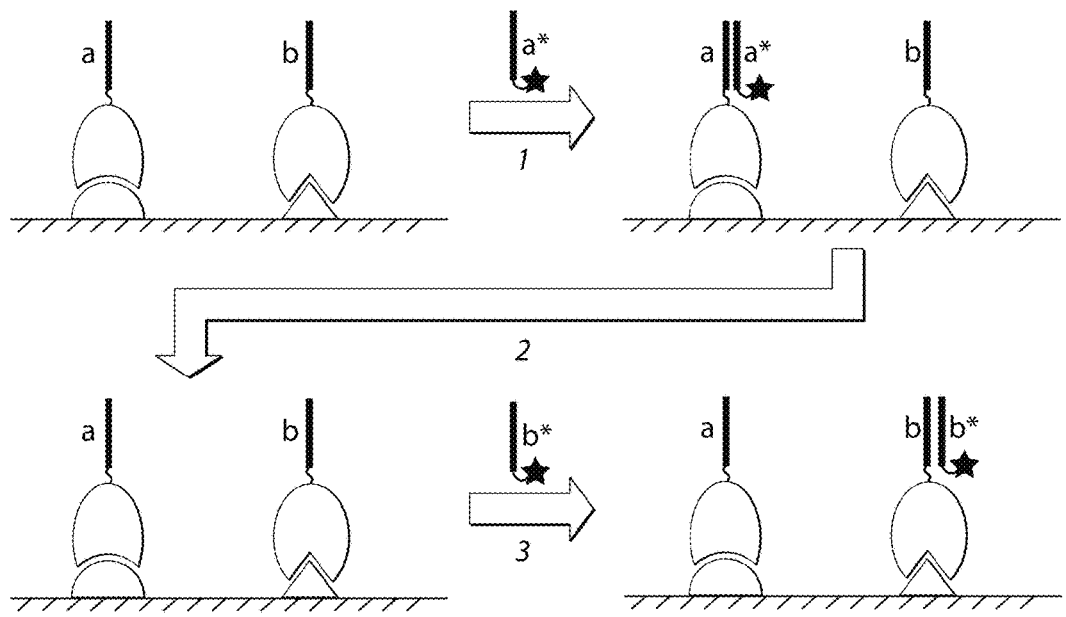
FIG. 3 is a schematic of one embodiment of inactivation of the imager strand by removing the imager strand using the methods provided in this disclosure.

To achieve imager nucleic acid inactivation in some of the methods provided herein, the imager nucleic acids, including the imager strands, may be removed from the target-recognition moieties, including the binding partners, (FIG. 3) by means such as but not limited to increasing temperature; decreasing the concentration of counter-ions (e.g., free Mg++); introducing or increasing the concentration of denaturants (e.g. formamide, urea, DMSO, and the like); and chemically, photochemically or enzymatically cleaving, modifying or degrading the imager strand, or any combination thereof.

Figure 4:
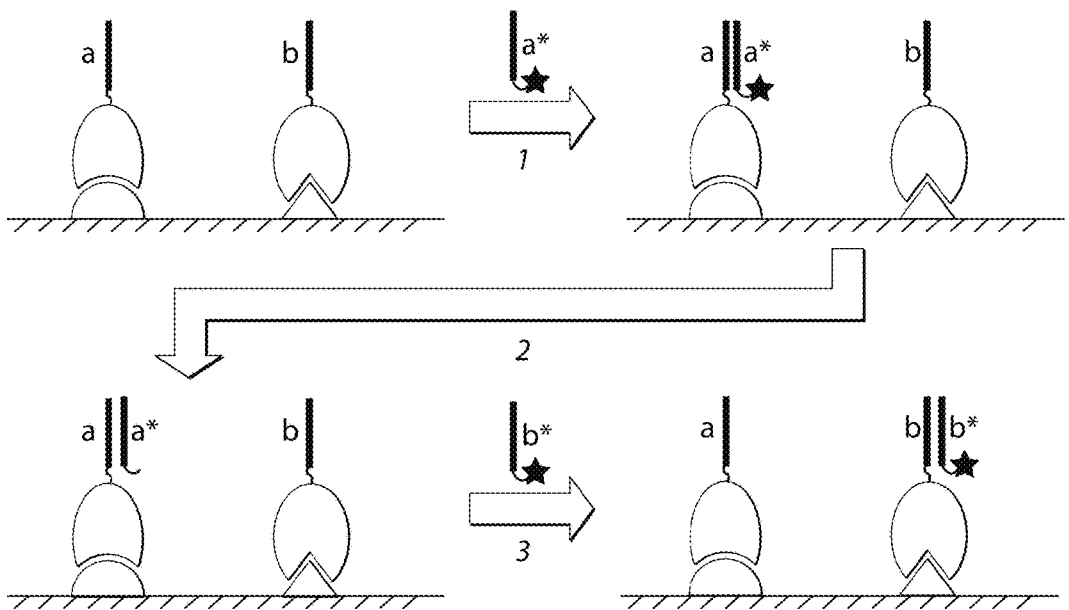
FIG. 4 is a schematic of one embodiment of inactivation of the imager strand by inactivating the fluorophore without removing the nucleic acid portion of the imager strand.

To achieve imager nucleic acid inactivation in some of the methods provided herein, the imager nucleic acids, including the imager strands, may be inactivated by removing and/or modifying the signal-emitting moiety without removing the entirety of the nucleic acid portion of the imager nucleic acid from the docking strands. (FIG. 4.)

As an example, the removal of the imager nucleic acid may be facilitated by cleaving the imager strand into multiple parts. In some embodiments, the imager nucleic acid comprises a chemically cleavable moiety that can be cleaved by introduction of the chemical compound that acts upon such cleavable moiety. Examples of such chemically cleavable moieties include but are not limited to allyl groups, which can be cleaved by certain Pd-based reagents (Ju J. et al., *Proc Natl Acad Sci USA.* 2006 Dec. 26; 103(52):19635-40, incorporated by reference herein); azido groups, which can be cleaved by certain phosphorous-based reagents such as TCEP (Guo J et al. *Proc Natl Acad Sci USA.* 2008 Jul. 8; 105(27):9145-50, incorporated by reference herein); bridging phosphorothiolates, which can be cleaved by silver-based reagents (Mag M. et al. *Nucleic Acids Res.* 1991 Apr. 11; 19(7):1437-41, incorporated by reference herein); disulfide bonds, which can be cleaved by reducing agents such as DTT and TCEP; and ribose, which can be cleaved by a variety of nucleophiles such as hydroxide and imidazole.

In some embodiments, the imager nucleic acid comprises a photocleavable linker that can be cleaved photochemically (e.g., by UV exposure). In some embodiments, the imager nucleic acid contains a moiety that can be cleaved by an enzyme. Examples of such enzymatically cleavable moieties include but are not limited to ribonucleotides, which can be cleaved by a variety of RNases; deoxyuridines, which can be cleaved by enzyme combinations such as USER (New England Biolabs); and restriction sites, which can be cleaved by sequence-specific nicking enzymes or restriction enzymes. In some embodiments, the restriction enzyme may cleave both the imager nucleic acid and the docking nucleic acid. In still other embodiments, the removal of the imager nucleic acid may be facilitated by modifying the imager nucleic acid into a form that binds the docking nucleic acid to form a duplex with decreased stability (or lower melting temperature).

As an example, the imager nucleic acid comprises azobenzene, which can be photoisomerized, wherein different isomers affect the binding strength of the imager nucleic acid to the docking nucleic acid differently (Asanuma H. et al. *Angew Chem Int Ed Engl.* 2001 Jul. 16; 40(14):2671-2673, incorporated by reference herein). In some embodiments, the imager nucleic acid comprises a deoxyuridine, in which the uracil group may be cleaved by uracil-DNA glycosylase. After the uracil is removed the binding strength of the imager strand is weakened.

Alternatively, the removal of the signal-emitting moiety can be achieved by cleaving a linker between the imager nucleic acid and the signal-emitting moiety, if such a linker exists. Chemistries described in herein can be used for this purpose as well.

The inactivation of the signal-emitting moiety can be achieved by chemically or photochemically modifying the signal-emitting moiety. For example, when the signal-emitting moiety is a fluorophore, it can be bleached by chemical agents (such as for example hydrogen peroxide, Gerdes M. et al. *Proc Natl Acad Sci USA.* 2013 Jul. 16; 110(29):11982-87, incorporated by reference herein) or photobleached (e.g., using soft multiwavelength excitation as described in Schubert W. et al. *Nat. Biotech.* 2006; 24:1270-78, incorporated by reference herein).

As will be understood in the art, "photobleaching" refers to the photochemical alteration of a dye or a fluorophore molecule such that it is unable to fluoresce. This is caused by cleavage of covalent bonds or non-specific reactions between the fluorophore and surrounding molecules. Loss of activity caused by photobleaching can be controlled, in some embodiments, by reducing the intensity or time-span of light exposure, by increasing the concentration of fluorophores, by reducing the frequency and thus the photon energy of the input light, or by employing more robust fluorophores that are less prone to bleaching (e.g. Alexa Fluors or DyLight Fluors). See, e.g., Ghauharali R. et al. *Journal of Microscopy* 2001; 198: 88-100; and Eggeling C. et al. *Analytical Chemistry* 1998; 70:2651-59.

Thus, photobleaching may be used to remove, modify or in some instance extinguish signal from a signal-emitting moiety. Photobleaching may be performed by exposing fluorophores to a wavelength of light of suitable wavelength, energy and duration to permanently and irreversibly extinguish the ability of the fluorophore to emit further signal. Photobleaching techniques are known in the art.

Figure 10:
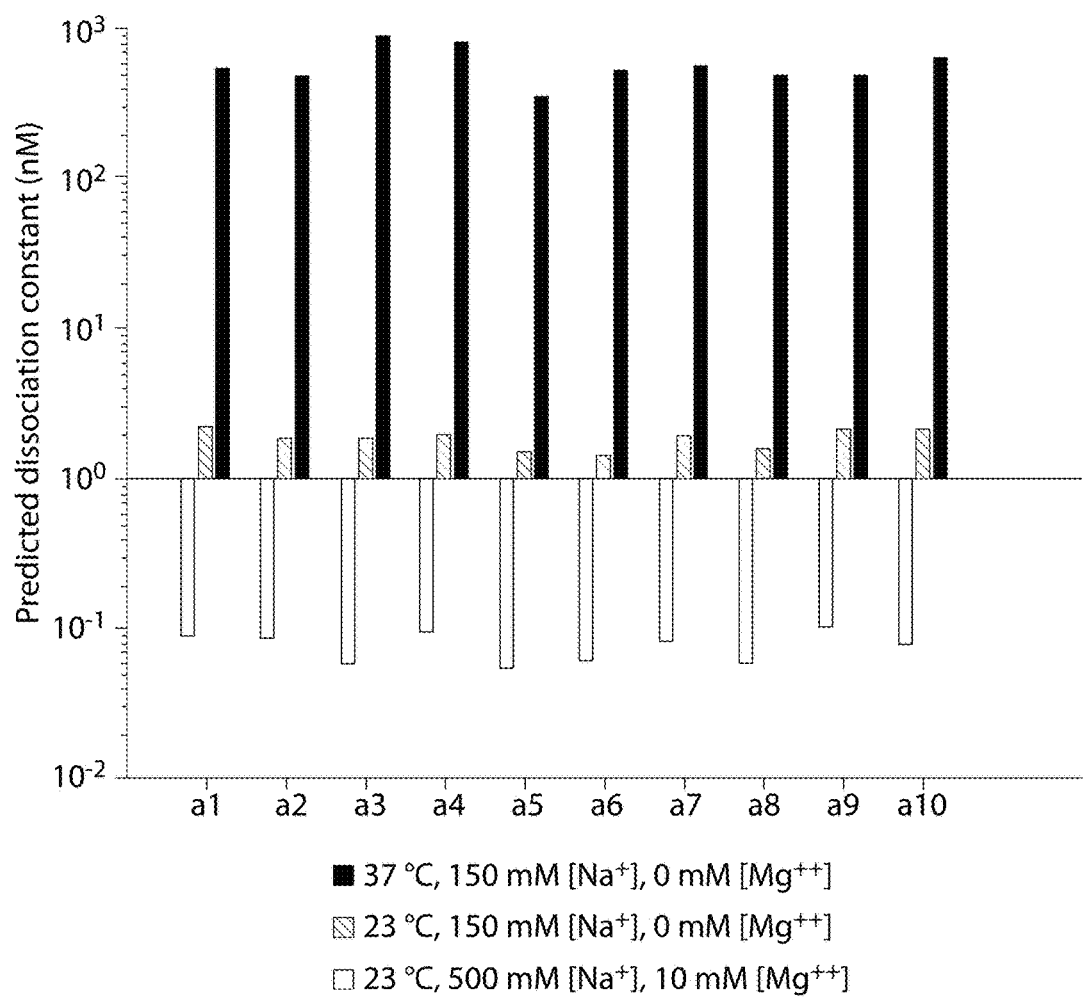
FIG. 10 is a graph showing the predicted dissociation constants of 10 different oligonucleotides with the respective reverse-complementary strands at 3 different conditions.

It was also found that, unlike antibodies that are generally able to bind their targets at a wide range of temperature below the physiological temperature (i.e., 0° C. to 37° C.) and can tolerate mild variation in salt concentration (i.e., monovalent cation concentration from 10 mM to 1 M; divalent cation from 0 to 10 mM), the affinity of short nucleic acid hybridization is dependent on temperature and salt concentration. For example, the predicted dissociation constant (using the parameter sets outlined in reference PMID 15139820) between ssDNA 5'-CATCTAAAGCC-3' and its reverse-complementary strand 5'-GGCTTTAGATG-3' is ~90 pM at 23° C. with 500 mM [Na+] and 10 mM [Mg++] concentration. In other words, in this condition the binding is very strong. The predicted dissociation constant of this pair of ssDNA is as high as ~500 nM at 37° C. with 150 mM [Na+] and 0 mM [Mg++]. In other words, in this condition the binding is fairly weak. The dissociation constants of these two conditions varies by nearly 4 orders of magnitude even though most antibodies are expected to bind their target strongly in both conditions. Similar trends are observed for other DNA sequences (FIG. 10). As a further example, the imaging condition can be 23° C. with 500 mM [Na+] and 10 mM [Mg++], and the dye-inactivating condition can be 37° C. with 150 mM [Na+] and 0 mM [Mg++].

In some embodiments, the sample being analyzed is cultured cells, tissue sections, or other samples from living organisms.

In some embodiments, the sample is dissociated cells that are immobilized to a solid surface (e.g. glass slide or cover slip), including individually immobilized. For example, the sample may be cells in blood. For example, the sample may contain cancer cells circulating in the blood (also known as circulating tumor cells, or CTCs). The sample may be cells grown in suspension. The sample may be cells disseminated from a solid tissue.

Sample

A "sample" may comprise cells (or a cell), tissue, or bodily fluid such as blood (serum and/or plasma), urine, semen, lymphatic fluid, cerebrospinal fluid or amniotic fluid. A sample may be obtained from (or derived from) any source including, without limitation, humans, animals, bacteria, viruses, microbes and plants. In some embodiments, a sample is a cell lysate or a tissue lysate. A sample may also contain mixtures of material from one source or different sources. A sample may be a spatial area or volume (e.g., a grid on an array, or a well in a plate or dish). A sample, in some embodiments, includes target(s), BP-NA conjugate(s) and imager strand(s). The cells may be disseminated (or dissociated) cells.

Target

A "target" is any moiety that one wishes to observe or quantitate and for which a binding partner exists. A target, in some embodiments, may be non-naturally occurring. The target, in some embodiments, may be a biomolecule. As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. Examples of biomolecules include, without limitation, DNA, RNA, cDNA, or the DNA product of RNA subjected to reverse transcription, A23187 (Calcimycin, Calcium Ionophore), Abamectine, Abietic acid, Acetic acid, Acetylcholine, Actin, Actinomycin D, Adenosine, Adenosine diphosphate (ADP), Adenosine monophosphate (AMP), Adenosine triphosphate (ATP), Adenylate cyclase, Adonitol, Adrenaline, epinephrine, Adrenocorticotropic hormone (ACTH), Aequorin, Aflatoxin, Agar, Alamethicin, Alanine, Albumins, Aldosterone, Aleurone, Alpha-amanitin, Allantoin, Allethrin, α-Amanatin, Amino acid, Amylase, Anabolic steroid, Anethole, Angiotensinogen, Anisomycin, Antidiuretic hormone (ADH), Arabinose, Arginine, Ascomycin, Ascorbic acid (vitamin C), Asparagine, Aspartic acid, Asymmetric dimethylarginine, Atrial-natriuretic peptide (ANP), Auxin, Avidin, Azadirachtin A—C35H44O16, Bacteriocin, Beauvericin, Bicuculline, Bilirubin, Biopolymer, Biotin (Vitamin H), Brefeldin A, Brassinolide, Brucine, Cadaverine, Caffeine, Calciferol (Vitamin D), Calcitonin, Calmodulin, Calmodulin, Calreticulin, Camphor—C10H16O, Cannabinol, Capsaicin, Carbohydrase, Carbohydrate, Carnitine, Carrageenan, Casein, Caspase, Cellulase, Cellulose—(C6H10O5), Cerulenin, Cetrimonium bromide (Cetrimide)—C19H42BrN, Chelerythrine, Chromomycin A3, Chaparonin, Chitin, α-Chloralose, Chlorophyll, Cholecystokinin (CCK), Cholesterol, Choline, Chondroitin sulfate, Cinnamaldehyde, Citral, Citric acid, Citrinin, Citronellal, Citronellol, Citrulline, Cobalamin (vitamin B12), Coenzyme, Coenzyme Q, Colchicine, Collagen, Coniine, Corticosteroid, Corticosterone, Corticotropin-releasing hormone (CRH), Cortisol, Creatine, Creatine kinase, Crystallin, α-Cyclodextrin, Cyclodextrin glycosyltransferase, Cyclopamine, Cyclopiazonic acid, Cysteine, Cystine, Cytidine, Cytochalasin, Cytochalasin E, Cytochrome, Cytochrome C, Cytochrome c oxidase, Cytochrome c peroxidase, Cytokine, Cytosine—C4H5N3O, Deoxycholic acid, DON (DeoxyNivalenol), Deoxyribofuranose, Deoxyribose, Deoxyribose nucleic acid (DNA), Dextran, Dextrin, DNA, Dopamine, Enzyme, Ephedrine, Epinephrine—C9H13NO3, Erucic acid—CH3(CH2)7CH═CH(CH2)11COOH, Erythritol, Erythropoietin (EPO), Estradiol, Eugenol, Fatty acid, Fibrin, Fibronectin, Folic acid (Vitamin M), Follicle stimulating hormone (FSH), Formaldehyde, Formic acid, Formnoci, Fructose, Fumonisin B1, Gamma globulin, Galactose, Gamma globulin, Gamma-aminobutyric acid, Gamma-butyrolactone, Gamma-hydroxybutyrate (GHB), Gastrin, Gelatin, Geraniol, Globulin, Glucagon, Glucosamine, Glucose—C6H12O6, Glucose oxidase, Gluten, Glutamic acid, Glutamine, Glutathione, Gluten, Glycerin (glycerol), Glycine, Glycogen, Glycolic acid, Glycoprotein, Gonadotropin-releasing hormone (GnRH), Granzyme, Green fluorescent protein, Growth hormone, Growth hormone-releasing hormone (GHRH), GTPase, Guanine, Guanosine, Guanosine triphosphate (+GTP), Haptoglobin, Hematoxylin, Heme, Hemerythrin, Hemocyanin, Hemoglobin, Hemoprotein, Heparan sulfate, High density lipoprotein, HDL, Histamine, Histidine, Histone, Histone methyltransferase, HLA antigen, Homocysteine, Hormone, human chorionic gonadotropin (hCG), Human growth hormone, Hyaluronate, Hyaluronidase, Hydrogen peroxide, 5-Hydroxymethylcytosine, Hydroxyproline, 5-Hydroxytryptamine, Indigo dye, Indole, Inosine, Inositol, Insulin, Insulin-like growth factor, Integral membrane protein, Integrase, Integrin, Intein, Interferon, Inulin, Ionomycin, Ionone, Isoleucine, Iron-sulfur cluster, K252a, K252b, KT5720, KT5823, Keratin, Kinase, Lactase, Lactic acid, Lactose, Lanolin, Lauric acid, Leptin, Leptomycin B, Leucine, Lignin, Limonene, Linalool, Linoleic acid, Linolenic acid, Lipase, Lipid, Lipid anchored protein, Lipoamide, Lipoprotein, Low density lipoprotein, LDL, Luteinizing hormone (LH), Lycopene, Lysine, Lysozyme, Malic acid, Maltose, Melatonin, Membrane protein, Metalloprotein, Metallothionein, Methionine, Mimosine, Mithramycin A, Mitomycin C, Monomer, Mycophenolic acid, Myoglobin, Myosin, Natural phenols, Nucleic Acid, Ochratoxin A, Oestrogens, Oligopeptide, Oligomycin, Orcin, Orexin, Ornithine, Oxalic acid, Oxidase, Oxytocin, p53, PABA, Paclitaxel, Palmitic acid, Pantothenic acid (vitamin B5), parathyroid hormone (PTH), Paraprotein, Pardaxin, Parthenolide, Patulin, Paxilline, Penicillic acid, Penicillin, Penitrem A, Peptidase, Pepsin, Peptide, Perimycin, Peripheral membrane protein, Perosamine, Phenethylamine, Phenylalanine, Phosphagen, phosphatase, Phospholipid, Phenylalanine, Phytic acid, Plant hormones, Polypeptide, Polyphenols, Polysaccharides, Porphyrin, Prion, Progesterone, Prolactin (PRL), Proline, Propionic acid, Protamine, Protease, Protein, Proteinoid, Putrescine, Pyrethrin, Pyridoxine or pyridoxamine (Vitamin B6), Pyrrolysine, Pyruvic acid, Quinone, Radicicol, Raffinose, Renin, Retinene, Retinol (Vitamin A), Rhodopsin (visual purple), Riboflavin (vitamin B2), Ribofuranose, Ribose, Ribozyme, Ricin, RNA—Ribonucleic acid, RuBisCO, Safrole, Salicylaldehyde, Salicylic acid, Salvinorin-A—C23H28O8, Saponin, Secretin, Selenocysteine, Selenomethionine, Selenoprotein, Serine, Serine kinase, Serotonin, Skatole, Signal recognition particle, Somatostatin, Sorbic acid, Squalene, Staurosporin, Stearic acid, Sterigmatocystin, Sterol, Strychnine, Sucrose (sugar), Sugars (in general), superoxide, T2 Toxin, Tannic acid, Tannin, Tartaric acid, Taurine, Tetrodotoxin, Thaumatin, Topoisomerase, Tyrosine kinase, Taurine, Testosterone, Tetrahydrocannabinol (THC), Tetrodotoxin, Thapsigargin, Thaumatin, Thiamine (vitamin B1)—C12H17ClN4OS.HCl, Threonine, Thrombopoietin, Thymidine, Thymine, Triacsin C, Thyroid-stimulating hormone (TSH), Thyrotropin-releasing hormone (TRH), Thyroxine (T4), Tocopherol (Vitamin E), Topoisomerase, Triiodothyronine (T3), Transmembrane receptor, Trichostatin A, Trophic hormone, Trypsin, Tryptophan, Tubulin, Tunicamycin, Tyrosine, Ubiquitin, Uracil, Urea, Urease, Uric acid—C5H4N4O3, Uridine, Valine, Valinomycin, Vanabins, Vasopressin, Verruculogen, Vitamins (in general), Vitamin A (retinol), Vitamin B, Vitamin B1 (thiamine), Vitamin B2 (riboflavin), Vitamin B3 (niacin or nicotinic acid), Vitamin B4 (adenine), Vitamin B5 (pantothenic acid), Vitamin B6 (pyridoxine or pyridoxamine), Vitamin B12 (cobalamin), Vitamin C (ascorbic acid), Vitamin D (calciferol), Vitamin E (tocopherol), Vitamin F, Vitamin H (biotin), Vitamin K (naphthoquinone), Vitamin M (folic acid), Wortmannin and Xylose.

In some embodiments, a target may be a protein target such as, for example, proteins of a cellular environment (e.g., intracellular or membrane proteins). Examples of proteins include, without limitation, fibrous proteins such as cytoskeletal proteins (e.g., actin, arp2/3, coronin, dystrophin, FtsZ, keratin, myosin, nebulin, spectrin, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins, C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins; cell adhesion proteins (e.g., cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones); receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins, major histocompatibility antigens and T cell receptors); nutrient storage/transport proteins (e.g., ferritin); chaperone proteins; and enzymes.

In some embodiments, a target may be a nucleic acid target such as, for example, nucleic acids of a cellular environment. As used herein with respect to targets, docking strands, and imager strands, a "nucleic acid" refers to a polymeric form of nucleotides of any length, such as deoxyribonucleotides or ribonucleotides, or analogs thereof. For example, a nucleic acid may be a DNA, RNA or the DNA product of RNA subjected to reverse transcription. Non-limiting examples of nucleic acids include coding or non-coding regions of a gene or gene fragment, loci (locus) defined from linkage analysis, exons, introns, messenger RNA (mRNA), transfer RNA, ribosomal RNA, ribozymes, cDNA, recombinant nucleic acids, branched nucleic acids, plasmids, vectors, isolated DNA of any sequence, isolated RNA of any sequence, nucleic acid probes, and primers. Other examples of nucleic acids include, without limitation, cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), locked nucleic acids ("LNA"), and nucleic acids with modified backbones (e.g., base- or sugar-modified forms of naturally-occurring nucleic acids). A nucleic acid may comprise modified nucleotides, such as methylated nucleotides and nucleotide analogs ("analogous" forms of purines and pyrimidines are well known in the art). If present, modifications to the nucleotide structure may be imparted before or after assembly of the polymer. A nucleic acid may be a single-stranded, double-stranded, partially single-stranded, or partially double-stranded DNA or RNA.

In some embodiments, a nucleic acid (e.g., a nucleic acid target) is naturally-occurring. As used herein, a "naturally occurring" refers to a nucleic acid that is present in organisms or viruses that exist in nature in the absence of human intervention. In some embodiments, a nucleic acid naturally occurs in an organism or virus. In some embodiments, a nucleic acid is genomic DNA, messenger RNA, ribosomal RNA, micro-RNA, pre-micro-RNA, pro-micro-RNA, viral DNA, viral RNA or piwi-RNA. In some embodiments, a nucleic acid target is not a synthetic DNA nanostructure (e.g., two-dimensional (2-D) or three-dimensional (3-D) DNA nanostructure that comprises two or more nucleic acids hybridized to each other by Watson-Crick interactions to form the 2-D or 3-D nanostructure).

The nucleic acid docking strands and imager strands described herein can be any one of the nucleic acids described above (e.g., DNA, RNA, modified nucleic acids, nucleic acid analogues, naturally-occurring nucleic acids, synthetic nucleic acids).

Compositions

Provided herein are compositions that comprise at least one or at least two (e.g., a plurality) BP-NA conjugate(s) (e.g., protein-nucleic acid conjugate(s)) of the invention. The BP-NA conjugates may be bound to a target of interest (e.g., biomolecule) and/or stable bound to a complementary fluorescently labeled imager strand. A composition may comprise a plurality of the same species or distinct species of BP-NA conjugates. In some embodiments, a composition may comprise at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ BP-NA conjugates. In some embodiments, a composition may comprise at least 10, 50, 100, 500, 1000, 2000, 3000, 4000, 5000, $10^4$, 50000, $10^5$, $10^5$, $10^6$, $10^7$, $10^8$, $10^9$, $10^{10}$, $10^{11}$ complementary fluorescently labeled imager strands. In some embodiments, a composition may contain 1 to about 200 or more distinct species of BP-NA conjugates and/or imager strands. For example, a composition may contain at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200 or more distinct species. In some embodiments, a composition may contain less than about 5 to about 200 distinct species of BP-NA conjugates and/or imager strands. For example, a composition may contain less than 5, 6, 7, 8, 9, 10, 15, 20, 25, 30, 35, 40, 45, 50, 55, 60, 65, 70, 75, 80, 85, 90, 95, 100, 125, 150, 175 or 200 distinct species.

It should be understood that the number of complementary fluorescently labeled imager strands imager stands in a composition may be less than, equal to or greater than the number of BP-NA conjugates in the composition.

Kits

The invention further provides kits comprising one or more components of the invention. The kits may comprise, for example, a BP-NA conjugate and/or a fluorescently labeled imager strands. The kits may also comprise components for producing a BP-NA conjugate or for labeling an imager strand. For example, the kits may comprise a binding partner (e.g., antibody), docking strands and intermediate linkers such as, for example, biotin and streptavidin molecules, and/or imager strands. The kits can be used for any purpose apparent to those of skill in the art, including, those described above.

The kits may include other reagents as well, for example, buffers for performing hybridization reactions. The kit may also include instructions for using the components of the kit, and/or for making and/or using the BP-NA conjugates and/or labeled imager strands.

Applications

The BP-NA conjugates (e.g., protein-nucleic acid conjugates or antibody-nucleic acid conjugates) of the invention can be used, inter alia, in any assay in which existing target detection technologies are used.

Typically assays include detection assays including diagnostic assays, prognostic assays, patient monitoring assays, screening assays, bio-warfare assays, forensic analysis assays, prenatal genomic diagnostic assays and the like. The assay may be an in vitro assay or an in vivo assay. The present invention provides the advantage that many different targets can be analyzed at one time from a single sample using the methods of the invention, even where such targets are spatially not resolvable (and thus spatially indistinct) using prior art imaging methods. This allows, for example, for several diagnostic tests to be performed on one sample.

The BP-NA conjugates can also be used to simply observe an area or region.

The methods of the invention may be applied to the analysis of samples obtained or derived from a patient so as to determine whether a diseased cell type is present in the sample and/or to stage the disease. For example, a blood sample can be assayed according to any of the methods described herein to determine the presence and/or quantity of markers of a cancerous cell type in the sample, thereby diagnosing or staging the cancer.

Alternatively, the methods described herein can be used to diagnose pathogen infections, for example infections by intracellular bacteria and viruses, by determining the presence and/or quantity of markers of bacterium or virus, respectively, in the sample. Thus, the targets detected using the compositions and methods of the invention may be either patient markers (such as a cancer marker) or markers of infection with a foreign agent, such as bacterial or viral markers.

The quantitative imaging methods of the invention may be used, for example, to quantify targets (e.g., target biomolecules) whose abundance is indicative of a biological state or disease condition (e.g., blood markers that are upregulated or down-regulated as a result of a disease state).

Further, the compositions and methods of the invention may be used to provide prognostic information that assists in determining a course of treatment for a patient. For example, the amount of a particular marker for a tumor can be accurately quantified from even a small sample from a patient. For certain diseases like breast cancer, overexpression of certain proteins, such as Her2-neu, indicate a more aggressive course of treatment will be needed.

The methods of the present invention may also be used for determining the effect of a perturbation, including chemical compounds, mutations, temperature changes, growth hormones, growth factors, disease, or a change in culture conditions, on various targets, thereby identifying targets whose presence, absence or levels are indicative of a particular biological states. In some embodiments, the present invention is used to elucidate and discover components and pathways of disease states. For example, the comparison of quantities of targets present in a disease tissue with "normal" tissue allows the elucidation of important targets involved in the disease, thereby identifying targets for the discovery/screening of new drug candidates that can be used to treat disease.

The sample being analyzed may be a biological sample, such as blood, sputum, lymph, mucous, stool, urine and the like. The sample may be an environmental sample such as a water sample, an air sample, a food sample and the like. The assay may be carried out with one or more components of the binding reaction immobilized. Thus, the targets or the BP-NA conjugates may be immobilized. The assay may be carried out with one or more components of the binding reaction non-immobilized. The assays may involve detection of a number of targets in a sample, essentially at the same time, in view of the multiplexing potential offered by the BP-NA conjugates and fluorescently labeled imager strands of the invention. As an example, an assay may be used to detect a particular cell type (e.g., based on a specific cell surface receptor) and a particular genetic mutation in that particular cell type. In this way, an end user may be able to determine how many cells of a particular type carry the mutation of interest, as an example.

Various Embodiments

This disclosure provides a variety of embodiments including but not limited to the following numbered embodiments:
1. A method comprising
   (1) contacting a sample being tested for the presence of one or more targets with one or more target-specific binding partners, wherein each target-specific binding partner is linked to a docking strand, and wherein target-specific binding partners of different specificity are linked to different docking strands,
   (2) optionally removing unbound target-specific binding partners,
   (3) contacting the sample with labeled imager strands having a nucleotide sequence that is complementary to a docking strand,
   (4) optionally removing unbound labeled imager strands,
   (5) imaging the sample to detect location and number of bound labeled imager strands,
   (6) extinguishing signal from the bound labeled imager strand, and
   (7) repeating steps (3)-(6), each time with a labeled imager strand having a unique nucleotide sequence relative to all other labeled imager strands.
2. The method of embodiment 1, wherein the sample is contacted with more than one target-specific binding partner in step (1).
3. The method of embodiment 1 or 2, wherein the target-specific binding partner is an antibody or an antibody fragment.
4. The method of any one of embodiments 1-3, wherein the labeled imager strands are labeled identically.
5. The method of any one of embodiments 1-3, wherein the labeled imager strands each comprise a distinct label.
6. The method of any one of embodiments 1-5, wherein the labeled imager strands are fluorescently labeled imager strands.
7. The method of any one of embodiments 1-6, wherein the one or more targets are proteins.

8. The method of any one of embodiments 1-7, wherein the sample is a cell, a cell lysate or a tissue lysate.
9. The method of any one of embodiments 1-8, wherein the sample is imaged in step (5) using confocal or epi-fluorescence microscopy.
10. The method of any one of embodiments 1-9, wherein extinguishing signal in step (6) comprises photobleaching.
11. A composition comprising
   a sample bound to more than one target-specific binding partners, each binding partner bound to a docking strand, and
   at least one docking strand stably bound to a labeled imager strand.
12. A method comprising
   (1) contacting a sample being tested for the presence of one or more targets with one or more target-specific binding partners, wherein each target-specific binding partner is linked to a docking nucleic acid, and wherein target-specific binding partners of different specificity are linked to different docking nucleic acids,
   (2) optionally removing unbound target-specific binding partners,
   (3) contacting the sample with labeled imager nucleic acids having a nucleotide sequence that is complementary to a docking nucleic acid,
   (4) optionally removing unbound labeled imager nucleic acids,
   (5) imaging the sample to detect location and number of bound labeled imager nucleic acids,
   (6) removing the bound labeled imager nucleic acids from the docking nucleic acids, and
   (7) repeating steps (3)-(6), each time with a labeled imager nucleic acid having a unique nucleotide sequence relative to all other labeled imager nucleic acids.
13. The method of embodiment 12, wherein the sample is contacted with more than one target-specific binding partner in step (1).
14. The method of embodiment 12 or 13, wherein the target-specific binding partner is an antibody or an antibody fragment.
15. The method of embodiment 12 or 13, wherein the target-specific binding partner is a natural or engineered ligand, a small molecule, an aptamer, a peptide or an oligonucleotide.
16. The method of any one of embodiments 12-15, wherein the labeled imager nucleic acids are labeled identically.
17. The method of any one of embodiments 12-15, wherein the labeled imager nucleic acids each comprise a distinct label.
18. The method of any one of embodiments 12-17, wherein the labeled imager nucleic acids are fluorescently labeled imager nucleic acids.
19. The method of any one of embodiments 12-18, wherein the one or more targets are proteins.
20. The method of any one of embodiments 12-19, wherein the sample is a cell, a cell lysate or a tissue lysate.
21. The method of any one of embodiments 12-20, wherein the sample is imaged in step (5) using confocal or epi-fluorescence microscopy.
22. The method of any one of embodiments 12-21, wherein the labeled imager nucleic acids are removed from the docking nucleic acids by decreasing salt concentration, addition of a denaturant, or increasing temperature.
23. The method of embodiment 22, wherein the salt is Mg++.
24. The method of embodiment 22, wherein the denaturant is formamide, urea or DMSO.
25. The method of any one of embodiments 12-21, wherein the labeled imager nucleic acids are not removed from the docking nucleic acids by strand displacement in the presence of a competing nucleic acid.
26. The method of any one of embodiments 12-21, wherein the labeled imager nucleic acids are removed from the docking nucleic acids by chemically, photochemically, or enzymatically cleaving, modifying or degrading the labeled imager nucleic acids.
27. The method of any one of embodiments 12-21, wherein, when the labeled imager nucleic acid is bound to its respective docking nucleic acid, there is no single-stranded region on the imager nucleic acid or the docking nucleic acid.
28. The method of any one of embodiments 12-21, wherein the labeled imager nucleic acid is not self-quenching.
29. The method of any one of embodiments 12-28, wherein the unbound docking nucleic acid is partially double-stranded.
30. The method of any one of embodiments 12-28, wherein the unbound imager nucleic acid is partially double-stranded.
31. The method of any one of embodiments 12-28, wherein the imager nucleic acid is a molecular beacon or comprises a hairpin secondary structure.
32. The method of any one of embodiments 12-27 and 29-31, wherein the imager nucleic acid is a molecular beacon or comprises a hairpin secondary structure that is self-quenching.
33. The method of any one of embodiments 12-28, wherein the imager nucleic acid is a hemiduplex.
34. The method of embodiment 33, wherein the hemiduplex is self-quenching.
35. The method of any one of embodiments 12-34, wherein the docking nucleic acid comprises a hairpin secondary structure.
36. The method of any one of embodiments 12-35, wherein the imager nucleic acid is bound to multiple signal-emitting moieties through a dendrimeric structure or a polymeric structure.
34. A method comprising
   (1) contacting a sample being tested for the presence of one or more targets with one or more target-specific binding partners, wherein each target-specific binding partner is linked to a docking nucleic acid, and wherein target-specific binding partners of different specificity are linked to different docking nucleic acids,
   (2) optionally removing unbound target-specific binding partners,
   (3) contacting the sample with labeled imager nucleic acids having a nucleotide sequence that is complementary to a docking nucleic acid,
   (4) optionally removing unbound labeled imager nucleic acids,
   (5) imaging the sample to detect location and number of bound labeled imager nucleic acids,
   (6) inactivating the bound labeled imager nucleic acids, by removing or modifying their signal-emitting moieties without removing the imager nucleic acid in its entirety, and
   (7) repeating steps (3)-(6), each time with a labeled imager nucleic acids having a unique nucleotide sequence relative to all other labeled imager nucleic acids.
35. The method of embodiment 34, wherein the sample is contacted with more than one target-specific binding partner in step (1).

36. The method of embodiment 34 or 35, wherein the target-specific binding partner is an antibody or an antibody fragment.
37. The method of embodiment 34 or 35, wherein the target-specific binding partner is a natural or engineered ligand, a small molecule, an aptamer, a peptide or an oligonucleotide.
38. The method of any one of embodiments 34-37, wherein the labeled imager nucleic acids are labeled identically.
39. The method of any one of embodiments 34-37, wherein the labeled imager nucleic acids each comprise a distinct label.
40. The method of any one of embodiments 34-39, wherein the labeled imager nucleic acids are fluorescently labeled imager nucleic acids.
41. The method of any one of embodiments 34-40, wherein the one or more targets are proteins.
42. The method of any one of claims 34-41, wherein the sample is a cell, a cell lysate or a tissue lysate.
43. The method of any one of embodiments 34-42, wherein the sample is imaged in step (5) using confocal or epi-fluorescence microscopy.
44. The method of any one of embodiments 34-43, wherein the unbound docking nucleic acid is partially double-stranded.
45. The method of any one of embodiments 34-43, wherein the unbound imager nucleic acid is partially double-stranded.
46. The method of any one of embodiments 34-45, wherein the imager nucleic acid is a molecular beacon or comprises a hairpin secondary structure.
47. The method of any one of embodiments 34-45, wherein the imager nucleic acid is a molecular beacon or comprises a hairpin secondary structure that is self-quenching.
48. The method of any one of embodiments 34-45, wherein the imager nucleic acid is a hemiduplex.
49. The method of embodiment 48, wherein the hemiduplex is self-quenching.
50. The method of any one of embodiments 34-49, wherein the docking nucleic acid comprises a hairpin secondary structure.
51. The method of any one of embodiments 34-50, wherein the imager nucleic acid is bound to multiple signal-emitting moieties through a dendrimeric structure or a polymeric structure.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising
   (1) contacting a sample being tested for the presence of one or more targets with one or more target-specific binding partners, wherein each target-specific binding partner is linked to a docking strand, and wherein target-specific binding partners of different specificity are linked to different docking strands to produce one or more targets bound to one or more target-specific binding partners,
   (2) optionally removing unbound target-specific binding partners,
   (3) contacting the sample with labeled imager strands that bind to docking strands,
   (4) optionally removing unbound labeled imager strands,
   (5) imaging the sample to detect bound labeled imager strands,
   (6) inactivating the bound labeled imager strands, by removing or modifying their signal-emitting moieties without removing the imager strand in its entirety, and
   (7) repeating at least some of steps (3)-(6) at least once with a labeled imager strand having a unique composition relative to at least one other labeled imager strand of step (3).

2. The method of claim 1, wherein the sample is contacted with more than one target-specific binding partner in step (1).

3. The method of claim 1, wherein the target-specific binding partner is an antibody or an antibody fragment.

4. The method of claim 1, wherein the target-specific binding partner is a ligand, a small molecule, an aptamer, a peptide or an oligonucleotide.

5. The method of claim 1, wherein the labeled imager strands are labeled identically.

6. The method of claim 1, wherein the labeled imager strands each comprise a distinct label.

7. The method of claim 1, wherein the labeled imager strands are fluorescently labeled imager strands.

8. The method of claim 1, wherein the one or more targets are proteins.

9. The method of claim 1, wherein the sample is a cell, a cell lysate or a tissue lysate.

10. The method of claim 1, wherein the sample is imaged in step (5) using confocal or epi-fluorescence microscopy.

11. The method of claim 1, wherein the unbound docking strand is partially double-stranded.

12. The method of claim 1, wherein the unbound imager strand is partially double-stranded.

13. The method of claim 1, wherein the imager strand is a molecular beacon or comprises a hairpin secondary structure.

14. The method of claim 1, wherein the imager strand is a molecular beacon or comprises a hairpin secondary structure that is self-quenching.

15. The method of claim 1, wherein the imager strand is a hemiduplex.

16. The method of claim 15, wherein the hemiduplex is self-quenching.

17. The method of claim 1, wherein the docking strand comprises a hairpin secondary structure.

18. The method of claim 1, wherein the imager strand is bound to multiple signal-emitting moieties through a dendrimeric structure or a polymeric structure.

19. The method of claim 1, wherein the removal or modification of the signal-emitting moieties in step (6) comprises cleaving a linker between the imager strand and the signal-emitting moiety.

20. The method of claim 1, wherein the removal or modification of the signal-emitting moieties in step (6) comprises chemically or photochemically modifying the signal-emitting moiety.

21. The method of claim 1, wherein the removal or modification of the signal-emitting moieties in step (6) comprises bleaching by chemical agents.

22. The method of claim 1, wherein the removal or modification of the signal-emitting moieties in step (6) comprises photobleaching.

* * * * *

UNITED STATES PATENT AND TRADEMARK OFFICE
CERTIFICATE OF CORRECTION

PATENT NO. : 10,190,151 B2
APPLICATION NO. : 15/934031
DATED : January 29, 2019
INVENTOR(S) : Peng Yin et al.

Page 1 of 1

It is certified that error appears in the above-identified patent and that said Letters Patent is hereby corrected as shown below:

In the Specification

Please replace the paragraph at Column 1, Lines 17-25, with the following paragraph:
--GOVERNMENT LICENSE RIGHTS
This invention was made with government support under OD007292, EB018659, and MH106011 awarded by National Institutes of Health, and N00014-13-1-0593 awarded by Department of Defense/Office of Naval Research, and 1317291 awarded by National Science Foundation. The government has certain rights in the invention.--

Signed and Sealed this
Fifth Day of May, 2020

Andrei Iancu
*Director of the United States Patent and Trademark Office*